US010335439B2

(12) United States Patent
Imagawa et al.

(10) Patent No.: US 10,335,439 B2
(45) Date of Patent: Jul. 2, 2019

(54) METHOD FOR PRODUCING HUMAN CORNEAL EPITHELIUM SHEET

(71) Applicants: JCR Pharmaceuticals Co., Ltd., Ashiya-shi, Hyogo (JP); Kyoto Prefectural Public University Corporation, Kamigyo-ku, Kyoto-shi, Kyoto (JP)

(72) Inventors: Kiwamu Imagawa, Hyogo (JP); Kenichi Maeda, Hyogo (JP); Yuki Hosoda, Hyogo (JP); Shuichi Yokoyama, Hyogo (JP); Naoki Okumura, Kyoto (JP); Noriko Koizumi, Kyoto (JP); Shigeru Kinoshita, Kyoto (JP)

(73) Assignees: JCR Pharmaceuticals Co., Ltd., Ashiya-shi, Hyogo (JP); Kyoto Prefectural Public University Corporation, Kyoto-shi, Kyoto (JP)

( * ) Notice: Subject to any disclaimer, the term of this patent is extended or adjusted under 35 U.S.C. 154(b) by 187 days.

(21) Appl. No.: 14/772,854

(22) PCT Filed: Mar. 9, 2014

(86) PCT No.: PCT/JP2014/056078
§ 371 (c)(1),
(2) Date: Sep. 4, 2015

(87) PCT Pub. No.: WO2014/142038
PCT Pub. Date: Sep. 18, 2014

(65) Prior Publication Data
US 2016/0008408 A1    Jan. 14, 2016

(30) Foreign Application Priority Data

Mar. 11, 2013  (JP) ................................ 2013-074258

(51) Int. Cl.
A61K 35/36   (2015.01)
A61L 27/38   (2006.01)
C12N 5/071   (2010.01)
C12N 5/079   (2010.01)

(52) U.S. Cl.
CPC .......... A61K 35/36 (2013.01); A61L 27/3813 (2013.01); C12N 5/0602 (2013.01); C12N 5/0621 (2013.01); A61L 2430/16 (2013.01); C12N 2501/15 (2013.01); C12N 2501/727 (2013.01); C12N 2501/999 (2013.01); C12N 2502/1352 (2013.01)

(58) Field of Classification Search
None
See application file for complete search history.

(56) References Cited

U.S. PATENT DOCUMENTS

2006/0153928 A1  7/2006  Kinoshita et al.
2006/0234911 A1 10/2006  Hoffmann et al.
2008/0026030 A1  1/2008  Kinoshita et al.
2008/0039940 A1  2/2008  Hashimoto et al.

FOREIGN PATENT DOCUMENTS

| CN | 1753697 A | 3/2006 |
| CN | 101014375 A | 8/2007 |
| EP | 1731177 A1 | 12/2006 |
| WO | WO 2004/078225 A1 | 9/2004 |
| WO | WO 2005/087286 A1 | 9/2005 |

OTHER PUBLICATIONS

Higa et al., Proliferation and Differentiation of Transplantable Rabbit Epithelial Sheets Engineered with or without an Amniotic Membrane Carrier, Investigative Ophthalmology & Visual Science, Feb. 2007, vol. 48, No. 2.*
Nakamura et al., Mucin-like Glycoprotein Secretion is Mediated by Cyclic-AMP and Protein Kinase C Signal Transduction Pathways in Rat Corneal Epithelium, Exp. Eye Res. (1998) 66, 513±519.*
Zhou et al, ROCK Inhibitor Y-27632 Increases the Cloning Efficiency of Limbal Stem/Progenitor Cells by Improving Their Adherence and ROS-Scavenging Capacity, Tissue Engineering: Part C, vol. 19, No. 7, 2013.*
Koizumi et al., "Amniotic Membrane as a Substrate for Cultivating Limbal Corneal Epithelial Cells for Autologous Transplantation in Rabbits," Cornea, 2000, 19(1):65-71.
Koizumi et al., "Cultivated Corneal Epithelial Transplantation for Ocular Surface Reconstruction in Acute Phase of Stevens-Johnson Syndrome," Archives of Ophthalmology, Feb. 2001, 119:298-300.
Koizumi et al., "Comparison of intact and denuded amniotic membrane as a substrate for cell-suspension culture of human limbal epithelial cells," Graefe's Arch. Clin. Exp. Ophthalmol., 2007 (online Apr. 13, 2006), 245:123-134.
Koizumi et al., "Cultivation of Corneal Epithelial Cells in Intact and Denuded Human Amniotic Membrane," Investigative Ophthalmology & Visual Science, Aug. 2000, 41(9):2506-2513.
Koizumi et al., "Ocular surface reconstruction, amniotic membrane, and cultivated epithelial cells from the limbus," Br. J. Ophthalmol., 2003, 87:1437-1439.
Koizumi et al., "Cultivated Corneal Epithelial Stem Cell Transplantation in Ocular Surface Disorders," The American Academy of Ophthalmology, 2001, 108:1569-1574.

(Continued)

Primary Examiner — Taeyoon Kim
Assistant Examiner — Srikanth Patury
(74) Attorney, Agent, or Firm — Foley & Lardner LLP

(57) ABSTRACT

[Problem] To provide a method for producing human corneal epithelial sheet, wherein the human corneal epithelial-derived cells obtained by culturing human corneal epithelial cells are cultured on an amnion substrate.
[Solution] A method for culturing human corneal epithelial cells using mesenchymal stem cells as the feeder cells; and a method for culturing human corneal epithelial cells using a medium containing a ROCK inhibitor, a phosphodiesterase inhibitor, a MAP kinase inhibitor and a TGF-β receptor inhibitor in various combinations.

16 Claims, 5 Drawing Sheets

(56) References Cited

OTHER PUBLICATIONS

Koizumi et al., "An Evaluation of Cultivated Corneal Limbal Epithelial Cells, Using Cell-Suspension Culture," Investigative Ophthalmology & Visual Science, Jul. 2002, 43(7):2114-2121.
Miyashita et al., "Effect of combination of ROCK inhibitor and KGF on epithelial sheet of limbus in co-culture system of serum-containing feeder," Japan Cornea Society Sokai Keratoplasty Society of Japan Program Shorokushu, 2012, 36-28, p. 59, P005, with English translation.
Omoto et al., "The Use of Human Mesenchymal Stem Cell-Derived Feeder Cells for the Cultivation of Transplantable Epithelial Sheets," Investigative Ophthalmology & Visual Science, May 2009, 50(5):2109-2115.
Yamaguchi et al., "cAMP stimulates the in vitro proliferation of renal cyst epithelial cells by activating the extracellular signal-regulated kinase pathway," Kidney International, 2000, 57(4):1460-1471.
Chen et al., "Rho/ROCK Signaling in Regulation of Corneal Epithelial Cell Cycle Progression," J. Invest. Opthalmol. Vis. Sci., 2008, 49:175-183.

\* cited by examiner

Enlarged figure of the surface of HE-stained human corneal epithelial sheet (observed at 100-fold magnification)

Enlarged figure of the cross-section surface of HE-stained human corneal epithelial sheet (observed at 200-fold magnification)

Enlarged figure of the surface of HE-stained human corneal epithelial sheet produced using the human corneal epithelial-derived cells obtained by the alternative method (observed at 100-fold magnification)

Enlarged figure of the surface of HE-stained human corneal epithelial sheet produced using the human corneal epithelial-derived cells obtained by the alternative method (observed at 200-fold magnification)

METHOD FOR PRODUCING HUMAN CORNEAL EPITHELIUM SHEET

FIELD OF INVENTION

The present invention relates to human corneal epithelial sheet used for transplantation, and in particular to a method for producing human corneal epithelial sheet by use of human corneal epithelial-derived cells obtained by culturing human corneal epithelial cells.

BACKGROUND TECHNOLOGY

Cornea, a transparent tissue comprising five cellular layers, i.e. corneal epithelium, Bowman membrane, corneal stromal layer, Descemet's membrane, and corneal endothelium from outside to inside in the order, contains no blood vessel but nerves. Corneal epithelium is the non-keratinized stratified squamous epithelium having a thickness of about 50 μm and constitutes a part of the ocular surface. It functions as a barrier which limits the penetration of substances and prevents the invasion of pathogen such as bacteria and fungi to the inside of cornea. Tight junctions existing between adjacent cells in the outermost layer play an important role in maintaining the barrier functions of the corneal epithelium.

Corneal epithelium has a regeneration ability. Even if epithelium is injured, corneal epithelial cells are supplied by corneal epithelial stem cells and then tight junctions between adjacent cells are regenerated, resulting in the recovery and the maintenance of the barrier functions.

Keratoplasty is prevalent as an effective treatment technique for a corneal disease caused by the irreversible impairment of the barrier functions of the corneal epithelium. There are two kinds of keratoplasties; one is a penetrating keratoplasty in which full-thickness cornea is transplanted, and the other is a keratoplasty in which part of the corneal tissue is transplanted. Because the penetrating keratoplasty has a problem such as vulnerability of eyeball caused by dissection of all the layers of cornea, the keratoplasty in which part of the corneal tissue is transplanted has been prevalent in recent years. As the partial corneal tissue transfer noted above, there are two kinds of surgical techniques, one is a lamellar keratoplasty in which part of the corneal stroma and corneal epithelium are simultaneously transplanted, and the other is an epithelium keratoplasty in which only corneal epithelium is transplanted. These techniques have already been established in clinical practice for patients with recurrent corneal dystrophy and the like.

Corneal epithelial stem cells differentiable into corneal epithelial cells exist in the fundus of the corneal limbal tissue. Therefore, if the corneal limbal tissue is injured, corneal epithelial stem cells are not supplied to repair corneal epithelial cells. Furthermore, when corneal epithelium becomes extensively damaged, it takes long to supply the needed volume of corneal epithelial cells from corneal epithelial stem cells to repair the damage. In addition, when Bowman's membrane which is extracellular matrix of corneal epithelial cells becomes damaged, corneal epithelial cells develop adhesive imperfection resulting in an insufficient volume of the cells on the corneal epithelium. Thus, when the condition in which barrier functions of the corneal epithelium are damaged is continuing due to the corneal epithelium being left unrepaired for several weeks, the ocular surface easily becomes infected with bacteria. Upon ocular surface being infected, the ocular surface is overlaid with conjunctival epithelium accompanying neovascularization, and inflammation occurs due to a migration of immune cells. Furthermore, corneal tissues are destroyed with enzymes secreted by bacteria, resulting in possible loss of vision. Thus, a disease caused by impairment or decrease of supply of corneal epithelial stem cells refers to corneal epithelial stem cell deficiency. Transplantation of corneal epithelium to cornea developing inflammation caused by corneal epithelial stem cell deficiency shows decreased survival rate due to the rejection.

Furthermore, corneal epithelium transplantation has the problem of donor shortage in which enough corneal epithelium to meet needs cannot be obtained for use in the transplantation. To overcome the donor shortage, a method for transplantation in which cell sheets obtained by culturing corneal epithelial cells in-vitro are transplanted onto the damaged area of the corneal epithelium has been proposed. In such a case where the human corneal epithelial sheets are transplanted onto the damaged area, inflammation at the site of transplantation also becomes a problem. Therefore, a method to transplant human corneal epithelial sheet with the amnion layer has been tried to suppress the inflammation, in which the sheet was formed on the amnion.

A method to form cell sheet on the amnion has been reported where pieces of corneal epithelial limbus taken from a healthy white rabbit were seeded on an amnion substrate (amnion from which amnion epithelial cells were stripped off and removed), and then were co-cultured with feeder cells (NIH-3T3 cells) (Non Patent Literature 1). It has been confirmed that human corneal epithelial sheet obtained as above had a layered structure morphologically similar to living corneal epithelium. Based on the clinical trial in which human corneal epithelial sheets have been transplanted to patients with refractory ocular-surface disorders, wherein the sheet was formed by a similar method using pieces of healthy human corneal epithelial limbus, it has showed that transplantation of the corneal epithelial sheet obtained as above was effective as a method to recover eye functions (Non Patent Literatures 2 and 3).

The other method to form cell sheets on the amnion has been reported where corneal epithelial cells which were obtained by enzymatically treating pieces of corneal epithelial limbus taken from a healthy white rabbit or human were suspended and seeded on an amnion substrate (amnion from which amnion epithelial cells were stripped off and removed), and then were co-cultured with feeder cells (NIH-3T3 cells) (Patent Literature 1 and Non Patent Literature 4). It also has been confirmed that human corneal epithelial sheet obtained as above had a layered structure morphologically similar to living corneal epithelium. In addition, induction of tight junction-related protein expression were confirmed by culturing cells whereby the cell surface was exposed to the atmosphere (air-lifting) during the culture process of human corneal epithelial sheets.

PRIOR ART LITERATURE

Patent Literature
Patent Literature 1: WO2004/078225
[Non Patent Literature]
Non Patent Literature 1: Koizumi N. et al., Cornea, 19, 65-71 (2000)
Non Patent Literature 2: Koizumi N. et al., Archives of Ophthalmology, 119, 298-300 (2001)
Non Patent Literature 3: Koizumi N. et al., the American Academy of Ophthalmology, 108, 1569-74 (2001)

Non Patent Literature 4: Koizumi N. et al., Invest Ophthalmol Vis Sci, 43, 2114-21 (2002)

SUMMARY OF INVENTION

Technical Problem

Based on the above background, the objective of the present invention is to provide a method for efficiently producing human corneal epithelial sheet having a stable quality.

Solution to the Problem

In a study for the above-mentioned object, the present inventors found that cells derived from human corneal epithelial cells could be cultured by using mesenchymal stem cells as the feeder cells with a medium containing a ROCK inhibitor, a phosphodiesterase inhibitor, a MAP kinase inhibitor and a TGF-β receptor inhibitor in various combinations and, in addition, human corneal epithelial sheet could be efficiently produced by culturing the human corneal epithelial cells obtained by the above culturing on the human amnion, and then completed the present invention. Thus the present invention provides the followings:

(1) A method for producing cells derived from human corneal epithelial cells, which comprises a process wherein, in a culture vessel separated into first and second chambers by a membrane having micropores that disallow cells to pass through, feeder cells are added to the first chamber and human corneal epithelial cells are added to the second chamber, said human corneal epithelial cells are cultured by using a first medium containing a ROCK inhibitor and a phosphodiesterase inhibitor, and then said human corneal epithelial cells are cultured by using a second medium containing a phosphodiesterase inhibitor, a MAP kinase inhibitor and a TGF-β receptor inhibitor.

(2) The method according to (1) set forth above, wherein said culture vessel is separated by the membrane having micropores into two chambers up and down, so as to form an upper chamber and a lower chamber.

(3) The method according to (2) set forth above, wherein said lower chamber is the first chamber and said upper chamber is the second chamber, and said human corneal epithelial cells are cultured on the membrane having micropores.

(4) The method according to (3) set forth above, wherein said human corneal epithelial cells are cultured on the membrane having micropores that disallow said cells to pass through and retained in said culture vessel without direct contact with the feeder cells.

(5) The method according to any one of (1) to (4) set forth above, wherein the ROCK inhibitor contained in said first medium is Y27632, the phosphodiesterase inhibitor contained in said first and second media is 3-isobutyl-1-methylxanthine, the MAP kinase inhibitor contained in said second medium is selected from SB203580, SB239063 and a combination thereof, and the TGF-β receptor inhibitor contained in said second medium is selected from SB431542, LY364947, A83-01 and a combination thereof.

(6) The method according to any one of (1) to (4) set forth above, wherein the ROCK inhibitor contained in said first medium is Y27632, the phosphodiesterase inhibitor contained in said first and second media is 3-isobutyl-1-methylxanthine, the MAP kinase inhibitor contained in said second medium is SB203580, and the TGF-β receptor inhibitor contained in said second medium is SB431542.

(7) The method according to (6) set forth above, wherein the concentrations of Y27632 contained in said first medium, 3-isobutyl-1-methylxanthine contained in said first and second media, SB203580 contained in said second medium, and SB431542 contained in said second medium are 1 to 20 μM, 50 to 150 μM, 0.2 to 2 μM, and 0.2 to 2 μM, respectively.

(8) The method according to (6) set forth above, wherein the concentrations of Y27632 contained in said first medium, 3-isobutyl-1-methylxanthine contained in said first and second media, SB203580 contained in said second medium, and SB431542 contained in said second medium are about 10 μM, about 100 μM, about 1 μM, and about 1 μM, respectively.

(9) The method according to any one of (1) to (8) set forth above, wherein said feeder cells are human mesenchymal stem cells.

(10) The method further comprising a step wherein the cells obtained by the method according to any one of (1) to (9) set forth above are frozen by suspending in a cell-freezing liquid, so as to obtain frozen cells.

(11) Cells derived from the human corneal epithelial cells which are obtained by the method according to any one of (1) to (10) set forth above.

(12) Cells derived from the frozen human corneal epithelial cells which are obtained by the method according to (10) set forth above.

(13) A method for producing human corneal epithelial sheet, which comprises a step wherein, after thawing the cells derived from the human corneal epithelial cells according to (11) set forth above, the cells derived from the human corneal epithelial cells according to (11) or (12) set forth above are cultured in a culture vessel containing feeder cells and on an amnion substrate which is placed on the membrane having micropores that disallow said feeder cells to pass through and retained in said culture vessel with a third medium containing a ROCK inhibitor, and then cultured by using a fourth medium containing a MAP kinase inhibitor and a TGF-β receptor inhibitor, so as to form cell layer comprising the cells derived from said human corneal epithelial cells on said amnion substrate, and a subsequent step wherein said cell layer is cultured by using said fourth medium in a condition where all or part of the surface of said cell layer is not covered with the medium.

(14) The method according to (13) set forth above, wherein said amnion substrate is placed in said culture vessel with the side stripping off the amnion epithelium facing upward.

(15) The method according to (13) or (14) set forth above, wherein said ROCK inhibitor contained in said third medium is Y27632, said MAP kinase inhibitor contained in said fourth medium is SB203580, and said TGF-β receptor inhibitor contained in said fourth medium is SB431542.

(16) The method according to (15) set forth above, wherein the concentrations of Y27632 contained in said third medium, SB203580 contained in said fourth medium, and SB431542 contained in said fourth medium are 1 to 20 μM, 0.2 to 2 μM, and 0.2 to 2 μM, respectively.

(17) The method according to (15) set forth above, wherein the concentrations of Y27632 contained in said third medium, SB203580 contained in said fourth medium, and SB431542 contained in said fourth medium are about 10 μM, 1 μM, and about 1 μM, respectively.

(18) The method according to any one of (13) to (17) set forth above, wherein said feeder cells are human mesenchymal stem cells.

(19) A human corneal epithelial sheet obtained by the method according to any one of (13) to (18) set forth above, which comprises said amnion substrate and the cells derived from said human corneal epithelial cells.

(20) The human corneal epithelial sheet according to (19) set forth above, wherein 95% or more of an area of the side stripping off the amnion epithelium of said amnion substrate is covered with the cell layer formed by the cells derived from said human corneal epithelial cells.

(21) The human corneal epithelial sheet according to (20) set forth above, wherein 90% or more of said cell layer has a layered structure comprising two or more cell layers.

(22) The human corneal epithelial sheet according to any one of (19) to (21) set forth above, wherein 98% or more of the cells derived from said human corneal epithelial cells is cytokeratin AE1/AE3-positive, and 80% or more is cytokeratin 12-positive.

(23) The human corneal epithelial sheet according to any one of (19) to (21) set forth above, wherein 99% or more of the cells derived from said human corneal epithelial cells is cytokeratin AE1/AE3-positive, and 85% or more is cytokeratin 12-positive.

(24) The human corneal epithelial sheet according to any one of (19) to (23) set forth above for treatment of a corneal disease.

(25) The human corneal epithelial sheet according to (24) set forth above, wherein said corneal disease is the disease caused by the irreversible impairment of the barrier functions of the corneal epithelium.

(26) The human corneal epithelial sheet according to (24) set forth above, wherein said corneal disease is selected from the group consisting of corneal dystrophy, Stevens-Johnson syndrome, chemical injury and corneal epithelial stem cell deficiency.

(27) A human corneal epithelial sheet wherein 99.5% or more of the surface area of an amnion substrate is covered with the cell layer formed by the cells derived from human corneal epithelial cells, 98% or more of the cells is cytokeratin AE1/AE3-positive, 80% or more of the cells is cytokeratin 12-positive, 95% or more of the cell layer has a layered structure comprising four or more cell layers, 90% or more of the surface area of the cell layer is covered with flattened cells, and the ratio of fibroblasts in the cell layer is less than 0.1%.

Effects of Invention

The present invention enables to provide stably the human corneal epithelial sheets which have a constant quality and can be transplanted to patients with a corneal disease such as recurrent corneal dystrophy, thus overcomes the donor shortage for corneal epithelium transplantation.

BRIEF DESCRIPTION OF FIGURES

FIG. 3 (2) is the FACS analysis diagram of cytokeratin 12-positive cells. The vertical axis represents the cell number, and the horizontal axis represents the fluorescence intensity derived from Alexa Fluor (registered trademark) 647 dye. (C) and (D) indicate the control and the fluorescence intensity of anti-cytokeratin 12 antibody-stained cells, respectively.

DETAILED DESCRIPTION OF THE INVENTION

Figure 1:
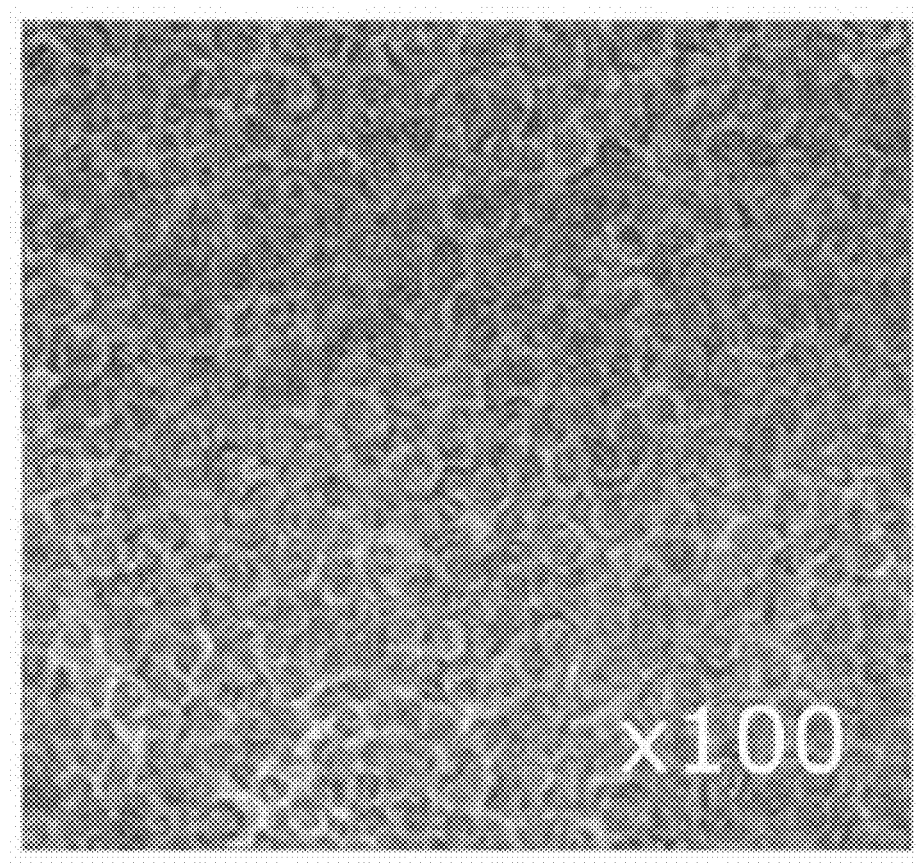
FIG. 1 is the enlarged figure of the surface of HE-stained human corneal epithelial sheet (observed at 100-fold magnification).

In a method for producing the cells derived from the human corneal epithelial cells in the present invention, the human corneal epithelial cells for use to produce the said cells are obtained by subjecting a corneal limbal tissue or a tissue slice containing human corneal epithelial tissue and corneal limbus to protease treatment. The corneal limbus is the site of transition from sclera to cornea, and contains the stem cells having differentiation potency to corneal epithelial cells. The protease used in this case is preferably dispase. The protease treatment preferably comprises a process wherein a tissue slice is treated by dispase first, and then the cells (or cell aggregation) are isolated from the surface of tissue slices to give the cell suspension. Dispase solution used in this case is PBS or the primary culture basal medium described later containing dispase at the concentration of preferably 0.5 to 2.0 U/mL.

Dispase treatment is performed by gentle shaking at 37° C. for 1 hour using a shaking apparatus or by allowing the cells to stand at 4° C. for 12 to 18 hours. Especially, when using the primary culture basal medium which contains dispase at the concentration of 0.5 to 2.0 U/mL as the dispase solution, the dispase treatment is carried out by allowing the cells to stand preferably at 4° C. for 12 to 18 hours followed by 37° C. for 40 to 80 minutes, more preferably at 4° C. for 14 to 16 hours followed by 37° C. for 50 to 70 minutes, and still more preferably at 4° C. for 15 to 20 hours followed by 37° C. for 60 minutes. CnT-20 (CELLnTEC) is preferably used as the primary culture basal medium.

In the present invention, in a culture vessel separated into first and second chambers by a membrane having micropores (support membrane) that disallow cells to pass through, adding feeder cells to the first chamber, the human corneal epithelial cells obtained by the protease treatment described above are cultured in the second chamber with the first medium containing a ROCK inhibitor, and then cultured by using the second medium containing a phosphodiesterase inhibitor, a MAP kinase inhibitor and a TGF-β receptor inhibitor. In the present invention, this series of culturing processes is referred to as the primary culture (P0 culture) of human corneal epithelial cells.

In one embodiment of the present invention, the human corneal epithelial cells obtained by the protease treatment described above are preferably cultured in the culture vessel containing the feeder cells and on the membrane (support membrane) which has micropores that disallow cells to pass through and is retained in the said culture vessel to avoid its lower side surface from the direct contact with the feeder cells with the first medium containing a ROCK inhibitor, and then cultured by using the second medium containing a phosphodiesterase inhibitor, a MAP kinase inhibitor and a TGF-β receptor inhibitor. In the same way described above, this series of culturing processes is referred to as the primary culture (P0 culture) of human corneal epithelial cells.

In the present invention, as long as mammal cells can be cultured, the culture vessel used to culture the human corneal epithelial cells and the feeder cells is not specifically limited, but is preferably a culture vessel in which cells can be cultured under adhesive state. The culture vessel is separated into first and second chambers by a membrane having micropores that disallow cells to pass through and is describe in detail later. The membrane disallows cells to pass through, so that there is no direct contact between the human corneal epithelial cells and the feeder cells without mixing them in the culture vessel. When the culture vessel has a flat bottom, the membrane may be vertically or horizontally placed on the bottom of the vessel. In a case where the membrane is vertically placed on the bottom, both the human corneal epithelial cells and the feeder cells are cultured on the bottom surface of the culture vessel. In a case where the membrane is horizontally placed on the flat bottom, either one of the human corneal epithelial cells and the feeder cells is cultured on the bottom surface of the culture vessel; the other is cultured on the membrane.

For example, commercially available cell culture plates (24-well plate, 12-well plate, 6-well plate and the like) may be used as a culture vessel having a flat bottom. The bottom of the culture vessel is preferably coated with cell-adhesive glycoproteins such as fibronectin, collagen (collagen types I, IV and the like) and laminin or peptides containing a cell-binding site (RGD sequence) of these glycoproteins to allow cells to adhere easily. When culturing NIH3T3 cells or human mesenchymal stem cells used as the feeder cells in this kind of culture vessel, the feeder cells adhere on the bottom of the vessel.

As described above, the inside of the culture vessel is separated into two chambers by the membrane having micropores and disallowing the feeder cells to pass through (support membrane), which is placed in the culture vessel. In a preferable embodiment, the membrane is placed inside of the culture vessel in such a way that the membrane is set roughly parallel to the bottom of the culture vessel, giving the culture space for the feeder cells on its downside and avoiding contact of the lower surface of the membrane with the feeder cells. Polyethylene terephthalate and polycarbonate are suitable for a material of support membrane. In particular, Polyethylene terephthalate is preferable. While the micropore in the membrane disallows the feeder cells (and the human corneal epithelial cells) to pass through, it allows a dissolved ingredient contained in the medium as a solute to pass through. The pore size of the micropore is preferably 0.1 to 1.5 µm, more preferably 0.2 to 1.2 µm, and still more preferably 0.4 to 1.0 µm. The size of the feeder cells (and the human corneal epithelial cells) is much larger than that of the micropore, so that the cells that are suspended in the medium cannot pass through the membrane, whereas dissolved ingredients such as the medium components and growth factors secreted by the feeder cells can pass through the membrane. Therefore, there is no direct contact between the corneal epithelial cells and the feeder cells in the culture vessel. The support membrane is preferably precoated with cell-adhesive glycoproteins such as fibronectin, collagen (collagen types I, IV and the like) and laminin or peptides containing a cell-binding site (RGD sequence) of these glycoproteins.

Figure 4:
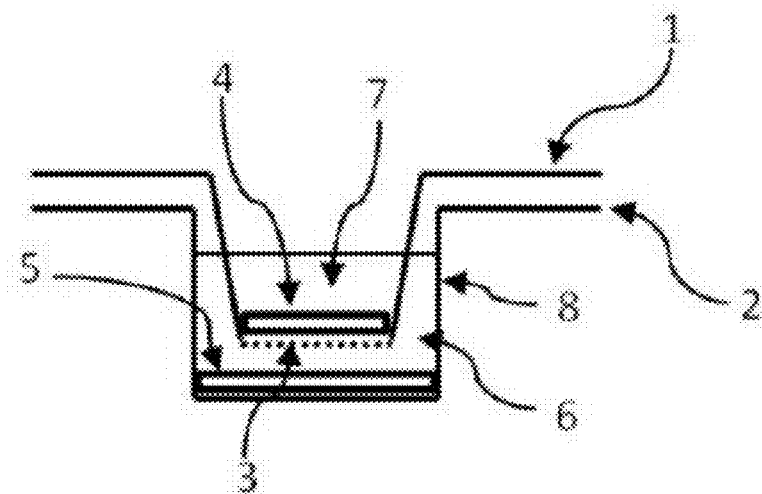
FIG. 4 is the schematic diagram of the setting of a culture vessel for the primary culture (P0 culture) of human corneal epithelial cells in working examples.

Based on the working examples, one example of the setting of a culture vessel for the primary culture of human corneal epithelial cells in the present invention is shown in FIG. 4 as a schematic diagram. As shown in FIG. 4, a culture vessel (6-well companion plate) is separated up and down by the membrane having micropores so as to give a lower chamber (the first chamber) and an upper chamber (the second chamber). Human mesenchymal stem cells as feeder cells are added to the first chamber, and human corneal epithelial cells are added to the second chamber. Human mesenchymal stem cells are cultured on the bottom surface of the culture vessel in the first chamber, and human corneal epithelial cells are cultured on the membrane having micropores in the second chamber. The cells cannot pass through the membrane having micropores, whereas liquid components such as the components of the medium and growth factors secreted by the feeder cells can pass through the micropore.

In the present invention, feeder cells mean the cells used to promote the proliferation of human corneal epithelial cells (or cells derived from human corneal epithelial cells) at the time of conducting the primary culture of human corneal epithelial cells (or cells derived from human corneal epithelial cells) or producing corneal epithelial sheet. The feeder cells have a function of promoting the proliferation of cells by replenishing nutrients which are insufficient in the medium, special growth factors and so on. As long as the feeder cells can promote the proliferation of human corneal epithelial cells (or cells derived from human corneal epithelial cells), cells that can be used as feeder cells are not specifically limited, but are preferably NIH3T3 cells, BALB/3T3 cells, Swiss 3T3 cells, mesenchymal stem cells and the like, more preferably mesenchymal stem cells and the like, and still more preferably mesenchymal stem cells. The feeder cells are more preferable to be the cells derived from human to prevent the contamination of foreign proteins.

In the present invention, mesenchymal stem cell (MSC) means the stem cell derived from mesenchyma or its precursor cell which is capable of proliferation in an undifferentiated state and differentiable into at least two types of cell. The cells differentiated and induced from mesenchymal stem cells, for example, are osteoblasts, chondroblasts and lipoblasts.

It has been known that MSC can be obtained from a variety of tissues including bone marrow, adipose tissue, dental pulp, umbilical blood, placenta, and amnion and so on. While either MSC can be used in the present invention as the MSC regardless of the tissue source, bone marrow-derived MSC is preferable. MSC used in the present invention is preferably human mesenchymal stem cell (hMSC).

hMSCs can be prepared in a variety of methods. For example, in the case of bone marrow-derived hMSCs, the hMSCs can be prepared by the method described in a patent literature (JP H07-500001) and so on.

The hMSCs used in the present invention can be further characterized by the expression pattern of surface antigens. When analyzed by a flow cytometry using specific antibodies, the hMSC is preferably positive for CD29, CD44 and CD105, and negative for CD34 and CD45; more preferably positive for CD29, CD44, CD73, CD90 and CD105, and negative for CD34 and CD45; still more preferably positive for CD29, CD44, CD73, CD90, CD105 and CD166, and negative for CD34 and CD45; and further more preferably positive for CD29, CD44, CD49a, CD49e, CD73, CD90, CD105 and CD166, and negative for CD34 and CD45.

The primary culture of human corneal epithelial cells is preferably conducted in such a way that the human corneal epithelial cells obtained by the protease treatment described above are added on the support membrane, resulting in that human corneal epithelial cells (or cells derived from human corneal epithelial cells) are present in the upper side of the support membrane, and the feeder cells are present in the lower side of the support membrane (the feeder cells being non-contact with the support membrane). During the cell culturing, medium is added to the vessel, so that the human corneal epithelial cells added on the support membrane are completely covered with the medium. In this case, the feeder cells are cultured on the bottom surface of the culture vessel, and the human corneal epithelial cells are cultured on the membrane having micropores (the support membrane). Regarding the support membrane, the lower side thereof with the feeder cells and the upper side thereof with the human corneal epithelial cells become the first chamber and the second chamber in the culture vessel, respectively. During the cell culturing, ingredients such as growth factors derived from the feeder cells are provided to the upper side of the support membrane through the micropore of the membrane. It is preferable that the human corneal epithelial cells are adhesively cultured on the surface of the support membrane.

In the present invention, the primary culture of human corneal epithelial cells may be conducted in such a way that human corneal epithelial cells (or cells derived from human corneal epithelial cells) are present in the lower side of the support membrane, and the feeder cells are present in the upper side of the support membrane as well. In this case, the feeder cells are cultured on the membrane having micropores, and the human corneal epithelial cells are cultured on the bottom surface of the culture vessel. It is preferable that the human corneal epithelial cells are adhesively cultured on the surface of the culture vessel. Regarding the support membrane, the upper side thereof with the feeder cells and the lower side of thereof with the human corneal epithelial cells become the first chamber and the second chamber in the culture vessel, respectively.

At the start of the primary culture (P0 culture), the human corneal epithelial cells are added on the surface of the culture vessel or on the support membrane in the culture vessel at the density of preferably $1 \times 10^4$ to $1 \times 10^5$ cells/cm$^2$, more preferably $4 \times 10^4$ to $6 \times 10^4$ cells/cm$^2$, and still more preferably about $5 \times 10^4$ cells/cm$^2$.

In the present invention, the term "cell" means the cell which extensively contains animal cells, especially both the feeder cell and human corneal epithelial cell (or cell derived from human corneal epithelial cell).

As the primary culture of human corneal epithelial cells, human corneal epithelial cells are cultured by using the first medium containing a ROCK inhibitor and then by using the second medium containing a phosphodiesterase inhibitor, a MAP kinase inhibitor and a TGF-β receptor inhibitor. The basal medium for the primary culture including the first and the second media contains amino acids, vitamins, inorganic salts and other ingredients. The sorts of the amino acids and their concentrations in the basal medium for the primary culture can be selected from Table 1 as needed.

TABLE 1

Amino acids and their concentrations in the medium for the primary culture

| Ingredients | Concentration range (mM) |
|---|---|
| Glycine | 0-12.8 |
| L-alanine | 0-3.4 |
| L-alanyl -L-glutamine | 0-1.2 |
| L-glutamine | 0-7 |
| L-arginine | 0.48-1.2 |
| L-asparagine | 0-1.2 |
| L-aspartic acid | 0-1.4 |
| L-cysteine | 0.08-0.7 |
| L-glutamic acid | 0-0.12 |
| L-histidine | 0.12-1.2 |
| L-isoleucine | 0.028-1.0 |
| L-leucine | 0.08-1.0 |
| L-lysine | 0.16-2.0 |
| L-methionine | 0.025-0.4 |
| L-phenylalanine | 0.025-0.5 |
| L-proline | 0-4.2 |
| L-serine | 0-0.3 |
| L-threonine | 0.08-0.96 |
| L-tryptophan | 0.008-0.095 |
| L-tyrosine | 0.024-0.48 |
| L-valine | 0.08-1.0 |
| L-cystein | 0.08-0.12 |

The sorts of the amino acids and their concentrations in the basal medium for the primary culture can be selected from Table 2 as needed.

TABLE 2

Vitamins and their concentrations in the basal medium for the primary culture

| Ingredients | Concentration range (mM) |
|---|---|
| biotin | 0-0.001 |
| choline chloride | 0.0056-0.12 |
| D-calcium pantothenate | 0.00032-0.01 |
| folic acid | 0.00036-0.011 |
| niacinamide | 0.00023-0.2 |
| pyridoxine | 0-0.024 |
| putrescine | 0.0001-0.001 |
| riboflavin | 0-0.0007 |
| vitamin B12 | 0-0.02 |
| myo- inositol | 0.0014-0.12 |
| ascorbic acid | 0-0.35 |
| DL-α tocopheryl phosphate | 0-0.0018 |
| 4-amino benzoic acid | 0-0.018 |
| thiamine hydrochloride | 0.0005-0.02 |

The sorts of the inorganic salts and their concentrations in the basal medium for the primary culture can be selected from Table 3 as needed.

TABLE 3

Inorganic salts and their concentrations in
the basal medium for the primary culture

| Ingredients | Concentration range (mM) |
|---|---|
| $CaCl_2 \cdot 2H_2O$ | 0-2.2 |
| $CuSO_4 \cdot 5H_2O$ | 0-0.000012 |
| $FeSO_4 \cdot 7H_2O$ | 0-0.0018 |
| $Fe(NO_3)_3 \cdot 9H_2O$ | 0-0.00015 |
| $MgCl_2 \cdot 6H_2O$ | 0-0.85 |
| $MgSO_4$ | 0-0.98 |
| KCl | 2.4-6.4 |
| $KH_2PO_4$ | 0-1.45 |
| $NaHCO_3$ | 1.1-54 |
| NaCl | 70-140 |
| $Na_2HPO_4$ | 0-1.2 |
| $NaH_2PO_4$ | 0-1.2 |
| $ZnSO_4 \cdot 7H_2O$ | 0-0.0036 |

Apart from the inorganic salts shown in Table 3, other inorganic salts such as sodium selenite, ammonium molybdate, manganese chloride, nickel sulfate, stannous chloride and sodium silicate can also be added to the medium as needed. In case of adding sodium selenite [$Na_2SeO_3$] to the medium, its concentration is preferably 0.003-0.02 mg/L, and more preferably about 0.005 mg/L. In case of adding ammonium molybdate [$(NH_4)_6Mo_7O_{24} \cdot 4H_2O$] to the medium, its concentration is preferably 0.0005-0.002 mg/L, and more preferably about 0.001 mg/L. In case of adding manganese chloride [$MnCl_2 \cdot 4H_2O$] to the medium, its concentration is preferably 0.0001-0.0004 mg/L, and more preferably about 0.0002 mg/L. In case of adding nickel sulfate [$NiSO_4 \cdot 6H_2O$] to the medium, its concentration is preferably 0.0001-0.0005 mg/L, and more preferably about 0.0003 mg/L. In case of adding stannous chloride [$SnCl_2 \cdot 2H_2O$] to the medium, its concentration is preferably 0.00005-0.0002 mg/L, and more preferably about 0.0001 mg/L. In case of adding sodium silicate [$Na_2SiO_3 \cdot 9H_2O$] to the medium, its concentration is preferably 0.0001-0.2 mg/L, and more preferably about 0.14 mg/L.

The sorts of the other ingredients and their concentrations in the basal medium for the primary culture can be selected from Table 4 as needed.

TABLE 4

Other ingredients and their concentrations
in the medium for the primary culture

| Ingredients | Concentration range (mM) |
|---|---|
| D-glucose | 4.5-67 |
| Hypoxanthine | 0-0.036 |
| linoleic acid | 0-0.00036 |
| lipoic acid | 0-0.0012 |
| phenol red | 0-0.0035 |
| thymidine | 0-0.0035 |
| calcium lactate | 0-3.1 |
| sodium acetate | 0-0.72 |
| HEPES | 0-18 |

Other ingredients in the basal medium for the primary culture can be selected from growth factors such as epidermal growth factor (EGF), basic fibroblast growth factor (bFGF), insulin and transferrin, adenine, L-ethanolamine, hydrocortisone, D,L-lipoic acid, sodium pyruvate, phosphorylethanolamine, heparin and adrenalin and so on, and the medium can be prepared by adding one or more of them as needed. In case of adding EGF to the medium, its concentration is preferably 1-50 ng/mL, and more preferably 5-40 ng/mL. In case of adding bFGF to the medium, its concentration is preferably 1-20 ng/mL, and more preferably 3-7 ng/mL. In case of adding insulin to the medium, its concentration is preferably 1-200 μg/mL, and more preferably 2-100 μg/mL. In case of adding transferrin to the medium, its concentration is preferably 1-200 μg/mL, and more preferably 2-20 μg/mL. In case of adding adenine to the medium, its concentration is preferably 15-35 mg/L, and more preferably 20-30 mg/L. In case of adding L-ethanolamine to the medium, its concentration is preferably 2.5-4 mg/L, and more preferably 3-3.5 mg/L. In case of adding hydrocortisone to the medium, its concentration is 0.1-1.0 mg/L, and more preferably 0.3-0.7 mg/L. In case of adding D,L-lipoic acid to the medium, its concentration is preferably 20-40 mg/L, and more preferably 25-30 mg/L. In case of adding sodium pyruvate to the medium, its concentration is preferably 40-65 mg/L, and more preferably 50-60 mg/L. In case of adding phosphorylethanolamine to the medium, its concentration is preferably 0.02-0.12 mg/L, and more preferably 0.05-0.10 mg/L. In case of adding heparin to the medium, its concentration is preferably 1-570 IU/L. In case of adding adrenalin to the medium, its concentration is preferably 0.1-2 μM.

As the basal medium for the primary culture, CnT-20 medium (CELLEnTEC) which is a serum-free medium for subculture of human corneal epithelia, can be preferably used. In addition, the basal medium for the primary culture can be prepared as needed according to the composition described in the patent documents 2000-506374 and 2000-517188 etc.

The first medium for the primary culture is the medium prepared by adding a ROCK inhibitor and a phosphodiesterase inhibitor to the basal medium for the primary culture. In this case, there is no limitation in the ROCK inhibitors added to the medium, but it is preferable to use Y27632 shown in the chemical structure (I). Its concentration in the medium is preferably 1-20 μM, and more preferably about 10 μM. In addition, in this case, there is no limitation in the phosphodiesterase inhibitors added to the medium, but 3-isobutyl-1-methylxanthine is preferably used. Its concentration in the medium is preferably 50-150 μM, and more preferably about 100 μM. Furthermore, two or more ROCK inhibitors and phosphodiesterase inhibitors can also be used in combination.

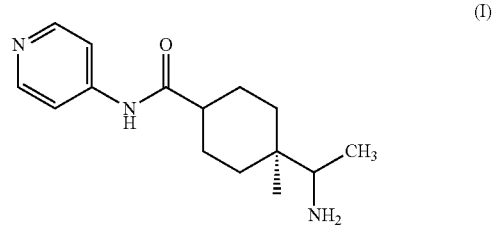

(I)

The second medium for the primary culture is the medium prepared by adding a phosphodiesterase inhibitor, a MAP kinase inhibitor and a TGF-β receptor inhibitor to the basal medium. In this case, there is no limitation in the phosphodiesterase inhibitors added to the basal medium of the primary culture, but 3-isobutyl-1-methylxanthine is used preferably. Its concentration is preferably 50-150 μM, and more preferably 100 μM. In addition, two or more phosphodiesterase inhibitors can also be used in combination.

In addition, there is no limitation for MAP kinase inhibitors added to the basal medium of the primary culture, but SB203580 shown in chemical structure (II) or SB239063 shown in chemical structure (III) are used preferably. In case of using SB203580, its concentration in the medium is preferably 0.2-2 μM, and more preferably about 1.0 μM. Furthermore, two or more MAP kinase inhibitors can also be used in combination.

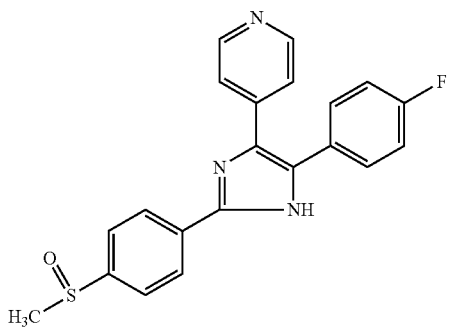

(II)

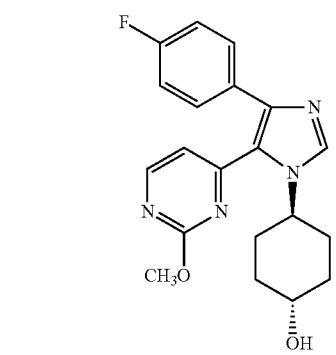

(III)

In addition, there is no limitation in TGF-β receptor inhibitors added to the basal medium of the primary culture, but SB431542 shown in the chemical structure (IV), LY364947 shown in the chemical structure (V) or A83-01 shown in the chemical structure (VI) are used preferably, and more preferably SB431542 and LY364947 are used. In case of use of SB431542, its concentration in the medium is preferably 0.2-2 μM, and more preferably about 1.0 μM. Furthermore, two or more TGF-β receptor inhibitors can also be used in combination.

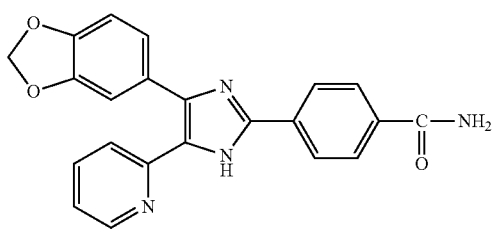

(IV)

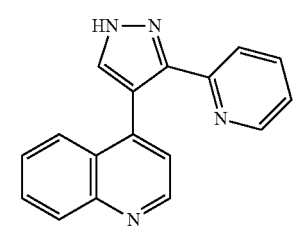

(V)

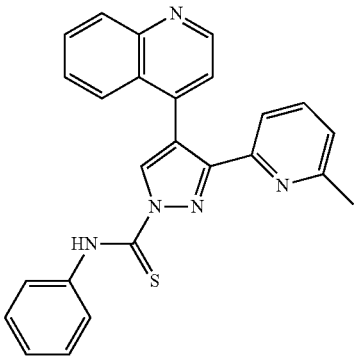

(VI)

In the present invention, cells proliferated and obtained by culturing human corneal epithelial cells correspond to the cells derived from human corneal epithelial cells (the human corneal epithelial-derived cells). The cells are also referred to as the human corneal epithelial cells for the sake of simplicity. The primary culture of human corneal epithelial cells is performed until the human corneal epithelial cells occupy preferably more than 70%, more preferably more than 85%, and still more preferably more than 90% of the surface of the support membrane. The cells obtained by the primary culture of human corneal epithelial cells can be used for producing human corneal epithelial sheet.

The human corneal epithelial cells obtained by the primary culture may be cryopreserved. Prior to the cryopreservation, the human corneal epithelial-derived cells on the culture vessel or the membrane are washed with PBS, and then treated with a proteolytic enzyme to detach the cells from the culture vessel or the membrane. The detached cells are suspended in a cryopreservation liquid, and then cryopreserved in liquid nitrogen. A proteolytic enzyme used in this case is preferably collagenase A.

The cryopreservation liquid used for cryopreservation of the human corneal epithelial-derived cells is, for example, dimethylsulfoxide (DMSO), fetal calf serum (FCS), natural polymer compounds or synthetic organic polymer compounds, monosaccharides or disaccharides, and aqueous solutions containing buffer solutions. Natural polymer compounds or synthetic organic polymer compounds, which are optional ingredients, are added to the cryopreservation liquid depending on the condition of the cells as needed. The concentration of DMSO contained in the cryopreservation liquid is preferably 5 to 15% (v/v). The concentration of the fetal calf serum contained in the cryopreservation liquid is preferably 50 to 90% (v/v). The natural polymer compound contained in the cryopreservation liquid is preferably dextran, glycogen, methylcellulose or carboxymethyl cellulose, and its concentration is preferably 0.1 to 1.0% (v/v). The synthetic organic polymer compound contained in the cryopreservation liquid is preferably polyethyleneglycol or polyvinylpyrrolidone, and its concentration is preferably 1 to 10% (v/v). The monosaccharide contained in the cryopreservation liquid is preferably glucose, and its concentration is preferably 1 to 10% (w/v). The disaccharide contained in the cryopreservation liquid is preferably sucrose, and its concentration is preferably 1 to 10% (w/v). A carbonate buffer solution, a phosphate buffer solution, HEPES and so on are preferably used as a buffer solution.

Preferable composition of the cryopreservation liquid is, for example, a composition of an aqueous solution containing 75% (v/v) of fetal calf serum, 10% (v/v) of DMSO, 3%

(w/v) of glucose, 0.08% (w/v) of sodium hydrogen carbonate, 0.036% (w/v) of HEPES, and 0.1575% (w/v) of RPMI1640 powder medium (powder). CELLBANKER (Nippon Zenyaku Kogyo Co., Ltd.) or CnT-CRYO-50 (CELLnTEC), a commercially available cryopreservation liquid, may be preferably used for cryopreservation of human corneal epithelial-derived cells.

The cell density of human corneal epithelial-derived cells in the cryopreservation liquid is preferably $0.5 \times 10^5$ to $1.5 \times 10^6$ cells/mL, and more preferably $1 \times 10^5$ to $1 \times 10^6$ cells/mL.

In the present invention, cryopreserved human corneal epithelial-derived cells may be used for producing human corneal epithelial sheet after thawing the cells. Thus, by cryopreserving and storing large amounts of the human corneal epithelial-derived cells, and then by thawing the cryopreserved cells as needed, the cells can be used for producing human corneal epithelial sheets. As a result, it becomes possible to stably supply the human corneal epithelial sheet.

In the present invention, the production of human corneal epithelial sheets is performed in such a way that the cells (the human corneal epithelial-derived cells) obtained by the primary culture of human corneal epithelial cells are cultured in a culture vessel containing feeder cells and on an amnion substrate which is placed on the membrane having micropores that disallow the feeder cells to pass through and retained in the culture vessel to avoid its lower side surface from the contact with the feeder cells with a third medium containing a ROCK inhibitor, and then cultured by using a fourth medium containing a MAP kinase inhibitor and a TGF-β receptor inhibitor.

The human corneal epithelial-derived cells which are not only cryopreserved and thawed by the method set forth above but also non-cryopreserved may be used for producing human corneal epithelial sheet. When using the non-cryopreserved human corneal epithelial-derived cells, the cells are detached from the support membrane by protease treatment after the completion of primary culture, and then suspended in the medium to use. A protease used in this case is preferably collagenase A.

For producing the human corneal epithelial sheet of the present invention, the human corneal epithelial-derived cells are cultured on an amnion substrate placed on the membrane (support membrane) which has micropores that disallow the feeder cells to pass through and is set inside of the culture vessel. The support membrane used is placed inside of the culture vessel in such a way that the membrane is set roughly parallel to the bottom of the culture vessel, giving the culture space for the feeder cells on its downside and avoiding contact of the lower surface of the membrane with the feeder cells. Polyethylene terephthalate and polycarbonate are suitable for a material of support membrane. In particular, Polyethylene terephthalate is preferable. While the micropore in the membrane disallows the feeder cells (and the human corneal epithelial cells) to pass through, it allows a dissolved ingredient contained in the medium as a solute to pass through. The pore size of the micropore is preferably 0.1 to 1.5 μm, more preferably 0.2 to 1.2 μm, and still more preferably 0.4 to 1.0 μm. The size of the feeder cells (and the human corneal epithelial cells) is much larger than that of the micropore, so that the cells that are suspended in the medium cannot pass through the membrane, whereas dissolved ingredients such as the medium components and growth factors secreted by the feeder cells can pass through the membrane. The support membrane is preferably pre-coated with fibronectin, collagen (collagen types I, IV and the like) and laminin and the like.

The amnion substrate used is prepared by stripping the epithelium off the amnion. The amnion substrate is spread with the side stripping off the epithelium facing upward to cover the whole surface of the support membrane, dried, and then immobilized on the support membrane. More specifically, amnion substrate is placed on the support membrane in the culture vessel with the side stripping off the amnion epithelium facing upward. The amnion used is preferably human amnion. The amnion may be air-dried.

For producing the human corneal epithelial sheet, the human corneal epithelial-derived cells are suspended in the medium, and then seeded on the amnion substrate immobilized on the support membrane at the density of preferably $1 \times 10^4$ to $2 \times 10^4$ cells/cm$^2$. During the cell culturing, the medium is added to the vessel, so that the human corneal epithelial cells added on the amnion substrate are completely covered with the medium. More specifically, the culturing is conducted in such a way that the feeder cells are present in the lower side of the membrane (the cells being non-contact with the membrane), and the amnion substrate and the human corneal epithelial-derived cells are present in the upper side of the membrane. During the cell culturing, ingredients such as growth factors derived from the feeder cells are provided to the upper side of the membrane through the micropores of the membrane.

For producing the human corneal epithelial sheet, the human corneal epithelial-derived cells seeded on the amnion substrate are cultured by using the third medium containing a ROCK inhibitor and a phosphodiesterase inhibitor. Basal medium for the third medium (basal medium for producing the human corneal epithelial sheet) contains amino acids, vitamins, inorganic salts and other ingredients. The sorts of the amino acids and their concentrations in the basal medium for producing the human corneal epithelial sheet can be selected from Table 5 as needed.

TABLE 5

Amino acids and their concentrations in the medium for the primary culture

| Ingredients | Concentration range (mM) |
| --- | --- |
| Glycine | 0-12.8 |
| L-alanine | 0-3.4 |
| L-alanyl -L-glutamine | 0-1.2 |
| L-glutamine | 0-7 |
| L-arginine | 0.48-1.2 |
| L-asparagine | 0-1.2 |
| L-aspartic acid | 0-1.4 |
| L-cysteine | 0.08-0.7 |
| L-glutamic acid | 0-0.12 |
| L-histidine | 0.12-1.2 |
| L-isoleucine | 0.028-1.0 |
| L-leucine | 0.08-1.0 |
| L-lysine | 0.16-2.0 |
| L-methionine | 0.025-0.4 |
| L-phenylalanine | 0.025-0.5 |
| L-proline | 0-4.2 |
| L-serine | 0-0.3 |
| L-threonine | 0.08-0.96 |
| L-tryptophan | 0.008-0.095 |
| L-tyrosine | 0.024-0.48 |
| L-valine | 0.08-1.0 |
| L-cystein | 0.08-0.12 |

The sorts of the vitamins and their concentrations in the basal medium for producing the human corneal epithelial sheet can be selected from Table 6 as needed.

TABLE 6

Vitamins and their concentrations in the
basic medium for the primary culture

| Ingredients | Concentration range (mM) |
|---|---|
| biotin | 0-0.001 |
| choline chloride | 0.0056-0.12 |
| D-calcium pantothenate | 0.00032-0.01 |
| folic acid | 0.00036-0.011 |
| niacinamide | 0.00023-0.2 |
| pyridoxine | 0-0.024 |
| putrescine | 0.0001-0.001 |
| riboflavin | 0-0.0007 |
| vitamin B12 | 0-0.02 |
| myo-inositol | 0.0014-0.12 |
| ascorbic acid | 0-0.35 |
| DL-α tocopheryl phosphate | 0-0.0018 |
| 4-amino benzoic acid | 0-0.018 |
| thiamine hydrochloride | 0.0005-0.02 |

The sorts of the inorganic salts and their concentrations in the basal medium for producing the human corneal epithelial sheet can be selected from Table 7 as needed.

TABLE 7

Inorganic salts and their concentrations in
the basal medium for the primary culture

| Ingredients | Concentration range (mM) |
|---|---|
| $CaCl_2 \cdot 2H_2O$ | 0-2.2 |
| $CuSO_4 \cdot 5H_2O$ | 0-0.000012 |
| $FeSO_4 \cdot 7H_2O$ | 0-0.0018 |
| $Fe(NO_3)_3 \cdot 9H_2O$ | 0-0.00015 |
| $MgCl_2 \cdot 6H_2O$ | 0-0.85 |
| $MgSO_4$ | 0-0.98 |
| KCl | 2.4-6.4 |
| $KH_2PO_4$ | 0-1.45 |
| $NaHCO_3$ | 1.1-54 |
| NaCl | 70-140 |
| $Na_2HPO_4$ | 0-1.2 |
| $NaH_2PO_4$ | 0-1.2 |
| $ZnSO_4 \cdot 7H_2O$ | 0-0.0036 |

In addition to the salts shown in Table 7, the inorganic salts such as sodium selenite, ammonium molybdate, manganese chloride, nickel sulfate, stannous chloride, and sodium silicate may be added to the medium as needed. In case of adding sodium selenite [$Na_2SeO_3$] to the medium, its concentration is preferably 0.003 to 02 mg/L, and more preferably about 0.005 mg/L. In case of adding ammonium molybdate [$(NH_4)_6Mo_7O_{24} \cdot 4H_2O$] to the medium, its concentration is preferably 0.0005 to 0.002 mg/L, and more preferably about 0.001 mg/L. In case of adding manganese chloride [$MnCl_2 \cdot 4H_2O$] to the medium, its concentration is preferably 0.0001 to 0.0004 mg/L, and more preferably about 0.0002 mg/L. In case of adding nickel sulfate [$NiSO_4 \cdot 6H_2O$] to the medium, its concentration is preferably 0.0001 to 0.0005 mg/L, and more preferably about 0.0003 mg/L. In case of adding stannous chloride [$SnCl_2 \cdot 2H_2O$] to the medium, its concentration is preferably 0.00005 to 0.0002 mg/L, and more preferably about 0.0001 mg/L. In case of adding sodium silicate [$Na_2SiO_3 \cdot 9H_2O$] to the medium, its concentration is preferably 0.0001 to 0.2 mg/L, and more preferably about 0.14 mg/L.

The sorts of the other ingredients and their concentrations in the basal medium for producing the human corneal epithelial sheet can be selected from Table 8 as needed.

TABLE 8

Other ingredients and their concentrations
in the medium for the primary culture

| Ingredients | Concentration range (mM) |
|---|---|
| Glucose | 4.5-67 |
| Hypoxanthine | 0-0.036 |
| linoleic acid | 0-0.00036 |
| lipoic acid | 0-0.0012 |
| phenol red | 0-0.0035 |
| thymidine | 0-0.0035 |
| calcium lactate | 0-3.1 |
| sodium acetate | 0-0.72 |
| HEPES | 0-18 |

The basal medium for producing the human corneal epithelial sheet preferably further comprises transferrin, hydrocortisone, adrenalin, insulin, epidermal growth factor (EGF) and the like. In the case that the medium contains transferrin, its concentration is preferably 1 to 200 μg/mL, and more preferably 3 to 5 μg/mL. In the case that the medium contains hydrocortisone, its concentration is preferably 0.8 to 1.4 mg/L, and more preferably 1.0 to 1.2 mg/L. In the case that the medium contains adrenalin, its concentration is preferably 0.1 to 2 μM, and more preferably 0.5 to 0.8 μM. In the case that the medium contains insulin, its concentration is preferably 1 to 200 μg/mL, and more preferably 3 to 7 μg/mL. In the case that the medium contains EFG, its concentration is preferably 1 to 50 ng/mL, and more preferably 5 to 40 ng/mL.

One or more of other ingredients selected from growth factors such as basic fibroblast growth factor (bFGF), adenine, L-ethanolamine, D,L-lipoic acid, sodium pyruvate, phosphorylethanolamine, heparin and so on may be added to the basal medium for producing the human corneal epithelial sheet as needed. In case of adding bFGF to the medium, its concentration is preferably 1 to 20 ng/mL, and more preferably 3 to 7 ng/mL. In case of adding adenine to the medium, its concentration is preferably 15 to 35 mg/L, and more preferably 20 to 30 mg/L. In case of adding L-ethanolamine to the medium, its concentration is preferably 2.5 to 4 mg/L, and more preferably 3 to 3.5 mg/L. In case of adding D,L-lipoic acid to the medium, its concentration is preferably 20 to 40 mg/L, and more preferably 25 to 30 mg/L. In case of adding sodium pyruvate to the medium, its concentration is preferably 40 to 65 mg/L, and more preferably 50 to 60 mg/L. In case of adding phosphorylethanolamine to the medium, its concentration is preferably 0.02 to 0.12 mg/L, and more preferably 0.05 to 0.10 mg/L. In case of adding heparin to the medium, its concentration is preferably 1 to 570 IU/L.

The medium obtained by mixing SHEM medium with KB medium in 1:2 ratio is preferably used as the basal medium for producing the human corneal epithelial sheet. In addition, fetal calf serum (FCS) may be added to the basal medium for producing the human corneal epithelial sheet. In case of adding fetal calf serum to the medium, its concentration is preferably 2 to 10%, and more preferably 4 to 6%.

The third medium for producing the human corneal epithelial sheet is the medium prepared by adding a ROCK inhibitor to the basal medium for producing the human corneal epithelial sheet. In this case, there is no particular limitation for the ROCK inhibitor added to the basal medium for producing the human corneal epithelial sheet, but Y27632 is preferably used. Its concentration in the medium is preferably 1 to 20 μM, and more preferably about 10 μM.

For producing the human corneal epithelial sheet, the culture period for the cell culture with the third medium is preferably 2 to 4 days, and more preferably 2 to 3 days.

Following the culture with the third medium, the human corneal epithelial-derived cells are cultured by using the fourth medium prepared by adding a MAP kinase inhibitor and a TGF-β receptor inhibitor to the basal medium for producing the human corneal epithelial sheet. In this case, there is no particular limitation for the MAP kinase inhibitor added to the basal medium for producing the human corneal epithelial sheet, but SB203580 is preferably used. When using SB203580, its concentration in the medium is preferably 0.2 to 2 μM, and more preferably about 1.0 μM. Furthermore, there is no particular limitation for the TGF-β receptor inhibitor added to the basal medium for producing the human corneal epithelial sheet, but SB431542 is preferably used. When using SB431542, its concentration in the medium is preferably 0.2 to 2 μM, and more preferably about 1.0 μM.

For producing the human corneal epithelial sheet, the culture period for the cell culture with the fourth medium is preferably 7 to 14 days. During the culture period, it is preferable that the medium is replaced every 2 days for 4 to 6 days from beginning of the culture, and then replaced every day for the following 7 to 14 days. After the final medium replacement, the medium is further replaced at the point where the lactic acid concentration in the medium is preferably 7 to 11 mM, and more preferably 8 to 10 mM while measuring the lactic acid concentration. By culturing the cells using the third and the fourth media, the cells are proliferated on the amnion substrate, resulting in the formation of cell layers comprising the cells derived from human corneal epithelial cells.

Following the culture with the fourth medium, the human corneal epithelial-derived cells are cultured preferably for 2 to 5 days, and more preferably for 3 days, under the condition in which the bottom of the amnion substrate is soaked in the medium, whereas all or part of the surface of the cell layer formed on the amnion substrate, comprising the cells derived from the human corneal epithelial-derived cells, is not covered with the medium (The condition in which the cell layer is exposed to the atmosphere in the culture vessel.). The culture method described above in which the surface of cultured cells is exposed to the atmosphere is referred to as air-lifting culture. The medium which can be used in the air-lifting culture is the medium prepared by adding a MAP kinase inhibitor and a TGF-β receptor inhibitor to the basal medium for producing the human corneal epithelial sheet, and is preferably the fourth medium.

During the air-lifting culture, the medium is preferably replaced every 10 to 24 hours, and more preferably replaced every 12 hours. Thus the human corneal epithelial sheet formed by the cell layer which comprises the human corneal epithelial-derived cells is obtained on the surface of the amnion substrate.

In the present invention, the human corneal epithelial sheet is the sheet covered with the cell layer which is formed by the human corneal epithelial-derived cells and on the side stripping off the amnion epithelium of the amnion substrate (the surface of the amnion substrate). In the present invention, the human corneal epithelial sheet is the sheet in which preferably 95% or more, more preferably 98% or more, still more preferably 99.5% or more, and more further preferably 99.8% or more of the surface of the amnion substrate is covered with the cell layer comprising the human corneal epithelial-derived cells, and preferably 90% or more, and more preferably 98% of the cell layer comprising the human corneal epithelial-derived cells has a layered structure comprising two or more cell layers. Furthermore, preferably 95% or more of the cell layer comprising the human corneal epithelial-derived cells has a layered structure comprising three or more cell layers. Moreover, preferably 95% or more of the cell layer comprising the human corneal epithelial-derived cells has a layered structure comprising four or more cell layers.

In the present invention, the human corneal epithelial sheet is the sheet in which preferably 90% or more, and more preferably 98% or more of the surface of the cell layer comprising the human corneal epithelial-derived cells is covered with flattened cells.

In the present invention, the ratio of fibroblasts in the cell layer formed on the surface of the amnion substrate, comprising the human corneal epithelial-derived cells, is preferably less than 0.1%, and more preferably less than 0.02%.

In the present invention, regarding the human corneal epithelial-derived cells forming the human corneal epithelial sheet, preferably 98% or more of the cells is cytokeratin AE1/AE3-positive and 80% or more of the cells is cytokeratin 12-positive, and more preferably 99% or more of the cells is cytokeratin AE1/AE3-positive and 85% or more of the cells is cytokeratin 12-positive.

The human corneal epithelial sheet produced in the present invention can be used for the treatment of patients with a corneal disease as an alternative for conventional keratoplasties.

As long as the disease caused by the impairment of the functions of corneal epithelium such as the barrier functions, corneal diseases for which the treatment with the human corneal epithelial sheet can be applied are not particularly limited, but especially the disease caused by the irreversible impairment of the functions of corneal epithelium such as the barrier functions such as recurrent corneal dystrophy, Stevens-Johnson syndrome, chemical injury and corneal epithelial stem cell deficiency.

WORKING EXAMPLES

While the present invention will be described in further detail below referring to examples, it is not intended that the present invention will be limited to the examples.

[Preparation of Feeder Cells]

Human mesenchymal stem cells (hMSC) which had been cryopreserved, were thawed quickly in an incubator at 37° C. After suspended by adding DMEM/10% FBS medium, the cells were collected by centrifugation. The cells thus collected were suspended with DMEM/10% FBS medium and the viable cell count was measured. The cells were then seeded on the bottom wells of cell culture insert companion plate, 6 wells (6-well companion plate, BD Biosciences) at the density of 15,000 to 25,000 cells/cm$^2$ and cultured in DMEM/10% FBS medium at 37° C. in existence of 5% $CO_2$ for 1 to 3 days. Immediately before the hMSC was used as the feeder cells for the primary culture (P0 culture) of human corneal epithelial cells, the DMEM/10% FBS medium was removed from the bottom wells. 1.5 mL of the medium, which was prepared by adding 10 μM of Y27632 (ROCK inhibitor, Sigma) and 100 μM of 3-isobutyl-1-methylxanthine (IBMX, phosphodiesterase inhibitor, Sigma) to CnT-20 medium which contains Supplement A, B and C, and 10 μg/mL gentamicin (Invitrogen) in the medium for culturing corneal epithelial cells (CELLnTEC), was added to the bottom wells. This was taken as the 6-well companion plate added with feeder cells.

[Primary Culture (P0 Culture) of Human Corneal Epithelial Cells]

From a human corneal tissue for laboratory use (a portion of two eyes, mfd. by SightLife), sclera and conjunctiva were removed under a microscope using scalpels and scissors, and tissue sections including corneal epithelial and limbal tissues were detached. To the detached tissue sections, PBS (Invitrogen) containing 1.2 U/mL dispase solution (Sanko Junyaku) was added and the mixture was shaken gently at 37° C. for 1 hour using a shaker. Then the enzymatic reaction was terminated by addition of PBS containing 0.02% EDTA and the tissue sections were transferred into a 35 mm dish (PrimeSurface, Sumitomo Bakelite). Human corneal epithelial cells were stripped off from the tissue sections using tweezers and the cell suspension was obtained. The suspension was transferred to an Eppendorf tube (PROTEOSAVE, Sumitomo Bakelite) followed by centrifugation. To the pellet of which the supernatant was removed, CnT-20 medium was added followed by centrifugation again and the cells were collected. The cells were suspended in 6 mL of CnT-20 medium containing 10 μM of Y27632 (ROCK inhibitor, Sigma) and 100 μM of 3-isobutyl-1-methylxanthine (IBMX, phosphodiesterase inhibitor, Sigma), which was designated as the first medium in working examples.

A 6-well cell culture insert (pore size: 0.4 μm, made from polyethylene terephthalate, BD Falcon Cell Culture Insert, mfd. by BD Biosciences) coated with FNC Coating Mix (Athena ES) as a feeder membrane was allowed to stand in the above 6-well companion plate added with feeder cells described above. To each well of the 6-well cell culture insert, 0.5 mL of each the suspension of the human corneal epithelial cells collected above (which equaled to 1/12 of the cells prepared from one eye) was added and the culture was started. 3 to 5 hours after the beginning of the culture, to the 6-well cell culture insert, 0.5 mL of CnT-20 medium containing 10 μM of Y27632 (a ROCK inhibitor, Sigma) and 100 μM of 3-isobutyl-1-methylxanthine (a IBMX, phosphodiesterase inhibitor, Sigma) was added and cultured further for 2 to 3 days. Then the medium was replaced with CnT-20 medium containing 100 μM of 3-isobutyl-1-methylxanthine (an IBMX, phosphodiesterase inhibitor, Sigma), 1 μM of SB203580 (a MAP kinase inhibitor, Sigma) and 1 μM of SB431542 (a TGF-β receptor inhibitor, Sigma), which was designated as the second medium in working examples. The cells were cultured by changing the medium every 2 to 3 days. If changes in the feeder cells in the bottom wells, such as significant stripping from the bottom wells, were observed during this period, another 6-well companion plate in which the feeder cells were adhered in the bottom wells would be prepared and the 6-well cell culture insert would be transferred to it to continue the culture. The culture of the cells including the following procedures was conducted at 37° C. in existence of 5% $CO_2$. The schema of the culture vessel setting in the primary culture of human corneal epithelial cells is shown in FIG. 4. The 6-well companion plate (the culture vessel) shown in FIG. 4, was separated into a lower side chamber (or the first chamber) and an upper side chamber (or the second chamber) by a membrane having micropores. To the first chamber human mesenchymal stem cells were added as feeder cells, while to the second chamber human corneal epithelial cells were added. The human mesenchymal stem cells adhered to the bottom of the culture vessel in the first chamber, while the human corneal epithelial cells were cultured in the second chamber on the surface of the membrane having micropores.

[Cryopreservation of the Human Corneal Epithelial-Derived Cells]

During the above primary culture of human corneal epithelial cells, when 90 to 100% of the surface of the 6-well culture insert (feeder membrane) was covered by the cells, the medium was changed and the culture was continued for 24 hours. Then the medium was discarded and PBS solution (G-PBS) containing gentamicin (Invitrogen) was added to the 6-well culture insert to make the concentration of 10 μg/mL. After the cells were washed, the G-PBS was added again and was allowed to stand at 37° C. for about 15 minutes. Then collagenase A (mfd. by Roche) was added to make the concentration of 1 mg/mL. The mixture was shaken gently at 37° C. for 1 to 2 hours using a shaker and the cells were detached from the 6-well culture insert. Then the enzymatic reaction was terminated by addition of PBS containing 0.02% EDTA and the cells were suspended. The suspension was then transferred into a centrifuge tube (STEMFULL, Sumitomo Bakelite) and the cells were collected by centrifugation. After the cells were suspended in CnT-20 medium, the viable cell count and the viability were measured. The cells were collected by centrifugation again. Then Cellbanker-1 (Nippon Zenyaku Kogyo Co., Ltd.) was added to make the cell concentration of about $1 \times 10^5$ cells/mL and the cells were suspended. 1 mL each of the cell suspension was dispensed into cryotubes (WHEATON). The tubes were kept in a freezing container (BICELL, Nihon Freezer Co., Ltd.) previously cooled down to 4° C. and moved to liquid nitrogen after kept frozen overnight in a freezer at −80° C.

[Preparation of an Amnion Substrate for Producing Human Corneal Epithelial Sheet]

To a mixture of DMEM (Gibco) and sterilized glycerin (1:1), gentamicin was added to make the concentration of 10 μg/mL. It was used as a stock solution for an amnion. The amnion purchased from Supporting Organization for Regenerative Medicine was put in a tray in a safety cabinet and immersed with G-PBS. Chorion was detached manually using fingers while wearing sterilized gloves and was then cut into small squares pieces of about 2 cm×2 cm. The pieces were put in the stock solution and stored at −80° C.

After thawing, the amnion was transferred to a 10 cm dish and washed twice with G-PBS to remove the stock solution. Then 0.02% EDTA/PBS was added and treated at 37° C. for over 2 hours. After washing twice with G-PBS, the epithelium of the amnion was detached using a cell scraper under a microscope. The amnion whose epithelium had been detached, the amnion substrate, was immersed in G-PBS solution and stored at 4° C.

[Production of Human Corneal Epithelial Sheet]

The human mesenchymal stem cells (hMSC) which had been cryopreserved, were thawed quickly in an incubator at 37° C. The cells were suspended in DMEM/10% FBS medium and collected by centrifugation. The cells thus collected were suspended with DMEM/10% FBS medium and the viable cell count was measured. The cells were seeded in the bottom wells of a 6-well companion plate (Corning) at the density of $1.5 \times 10^4$ to $2.5 \times 10^4$ cells/cm$^2$ and cultured in DMEM/10% FBS medium for 1 to 3 days. Immediately before the hMSC was used as the feeder cells in the production of human corneal epithelial sheet, the DMEM/10% FBS medium was removed. After washing with PBS, 1.5 mL of the KB+SHEM medium containing 10 μM of Y27632 (a ROCK inhibitor, Sigma) was added and it was taken as the 6-well companion plate added with the feeder cells. The so-called KB+SHEM medium refers to a medium produced by the following method which is mixed by KB medium and SHEM medium at the ratio of 2:1. The KB medium is produced by adding 6 of the 7 kinds of attached additive agents except the extract of bovine pituitary gland (BPE), which includes 0.2% (v/v) OcuFactor Lifefactor, 5 μg/mL transferrin, 0.18 μg/mL hydrocortisone, 1 μM of adrenalin, 6 mM of L-glutamine and 5.0 μg/mL recombined human insulin to serum-free liquid medium for proliferating normal human corneal epithelial cells (LIFE-LINE Cell Technoligy) and further adding with gentamicin to make its concentration of 10 μg/mL. Meanwhile, the SHEM medium is produced by adding 5 μg/mL recombined human insulin, 10 ng/mL recombined human EGF (Gibco) and 10% FBS (Hyclone) to DMEM/F-12 (Gibco), and further adding with gentamicin to make its concentration of 10 μg/mL.

The amnion whose epithelium had been detached (amnion substrate) was transferred to a 6-well cell culture insert (Transwell Clear TM, pore size: 3 μm, made of polyester, Corning Inc.) so that its upper side was the one whose epithelium had been detached. It was spread under a microscope to cover the 6-well cell culture insert completely using a tweezer. After the amnion substrate was air-dried for a few minutes, an O-ring (DuPont) was inserted into the 6-well cell culture insert to fix the amnion substrate so that it could not move in the 6-well culture insert. After confirming under a microscope that no wrinkles, bubbles or micropores were on the culture surface, it was allowed to stand in the bottom wells of the 6-well companion plate added with feeder cells.

Then the human corneal epithelial-derived cells which had been cryopreserved above were thawed quickly in an incubator at 37° C. and suspended by adding the KB+SHEM medium. The cells were collected by centrifugation and then suspended in the KB+SHEM medium containing 10 μM of Y27632 (ROCK inhibitor, Sigma). The viable cell count of the cell suspension was measured.

The suspension of the human corneal epithelial-derived cells was added to a 6-well cell culture insert so that the viable cell count on the amnion substrate was over $1 \times 10^4$ cells/cm$^2$ and the culture was started. The upper limit of the quantity of the cell suspension added was 0.5 mL. 3 to 5 hours after the beginning of the culture, 0.5 mL of the KB+SHEM medium containing 10 μM of Y27632 (the third medium in working examples) was added further to the 6-well cell culture insert and cultured for 2 to 3 days.

Then, the 6-well cell culture insert and the medium in the bottom wells were discarded and the medium was replaced with the KB+SHEM medium (KB+SHEM culture medium, the fourth medium in working examples) containing 1 μM of SB203580 (Sigma) and 1 μM of SB431542 (Sigma). The cells were cultured for 4 to 6 days while replacing the medium with the fresh one (KB+SHEM culture medium) every 2 days, and then cultured for 7 to 14 days while replacing the medium every day. During this period, if changes in the feeder cells in the bottom wells, such as significant detaching from the bottom wells, were observed during this period, another 6-well companion plate in which the feeder cells were adhered in the bottom wells was prepared and the 6-well cell culture insert was transferred to it to continue the culture. The cells were proliferated on the amnion substrate and the cell layer composed of the human corneal epithelial-derived cells was formed.

The determination of the concentration of lactic acid in the culture supernatants was started 24 hours after the last medium change. When the concentration was over 8 to 10 mM, the 6-well cell culture insert and the medium in the bottom wells were discarded. Then 1.4 mL of the medium (KB+SHEM culture medium) was added to the bottom wells. The bottom of the amnion substrate which was put on the 6-well culture insert was immersed in the medium, while the surface of the cell layer of the cells derived from human corneal epithelial cells formed on the amnion substrate in the 6-well culture insert was completely or partly covered by the medium (but the surface of the cell layer was not dry.). The culture was continued for 3 days in such state that the surface of the cell layer was completely or partly exposed to the atmosphere in the culture vessel. The medium was changed five times at frequency of every 12 hours. The culture which is conducted when the surface of cell layer is not completely or partly covered by medium is called air-lifting culture.

After the culture, the sheet comprised by the amnion substrate and the layer of the human corneal epithelial-derived cells formed on the amnion substrate, which was formed on the 6-well cell culture insert, was taken as the human corneal epithelial sheet. Its quality evaluation was conducted by HE staining and FACS analysis.

[Division of Human Corneal Epithelial Sheet]

After culturing, the human corneal epithelial sheet was washed three times with the KB+SHEM culture medium on the 6-well cell culture insert. Then the sheet was divided into a ½ sheet and two ¼ sheets using a biopsy trepan and a scalpel.

[HE Staining]

After the division, the ½ sheet was fixed by a Super Fix (Kurabo) for 10 minutes. The Super Fix was removed and the sheet was washed three times with PBS. Then it was stained with Mayer's Hematoxylin solution (Wako Pure Chemical Industries Ltd.) for 30 minutes. After the Mayer's Hematoxylin solution was removed, it was washed three times with PBS. After confirming that the cell nucleus had been stained by Mayer's Hematoxylin solution, the sheet was then stained for 10 seconds using eosin Y solution (Wako Pure Chemical Industries Ltd.) which was a 5-fold dilution with PBS. Then eosin Y solution was removed and the sheet was washed three times with PBS. After confirming that the cytoplasm had been stained by eosin Y solution, the cell sheet was detached from the feeder membrane on the slide glass and was sealed in a cover glass using PBS. The surface of the human corneal epithelial sheet was observed under a microscope. The scope of the layer of the human corneal epithelial-derived cells (the layer of the cultured cells) and the existence of fibroblast were also observed.

In addition, the divided ¼ sheet was embedded in a Tissue-Tek (registered trademark) O.C.T. Compound (Sakura Finetech Japan) and sliced. The slice was stuck on a slide glass. The slide glass, on which the slice was stuck, was immersed in a slide stain tray added with Super Fix (Kurabo) for 10 minutes. After the cells were fixed, it was washed with tap water for 10 minutes. Then it was immersed in a slide stain tray added with Mayer's Hematoxylin solution for 45 seconds and washed with tap water for 10 minutes. After confirming that the cytoplasm had been stained, it was then stained for 10 seconds by eosin Y solution (Wako Pure Chemical Industries Ltd.) and washed with tap water for 10 minutes. After confirming that the cytoplasm had been stained by the eosin Y solution, it was immersed respectively, in slide stain trays in the order of 70, 80, 90, 95% ethanol for 10 minutes each. Then it was immersed in a tray containing xylene for 10 minutes. At last, the slide glass was taken out, air-dried and sealed in a cover glass with EUKITT (O. Kindler GmbH). It was used for observing the cross section of the human corneal epithelial sheet and the formation of multiple layer and squamous cells.

[The Results of HE Staining]

No fibroblast was confirmed as the result of the observation of the surface of human corneal epithelial sheet under a microscope (FIG. 1). Since there were at least 1000 cells in the visual field of the microscope, the ratio of the fibroblast in the human corneal epithelial-derived cells was less than 0.1%. In addition, it was found that in the visual field of the microscope, more than 98% of the area of the surface of the amnion substrate was covered by the layer of cultured cells and more than 90% of the layer of cultured cells had the layered structures with more than double layers.

Figure 2:
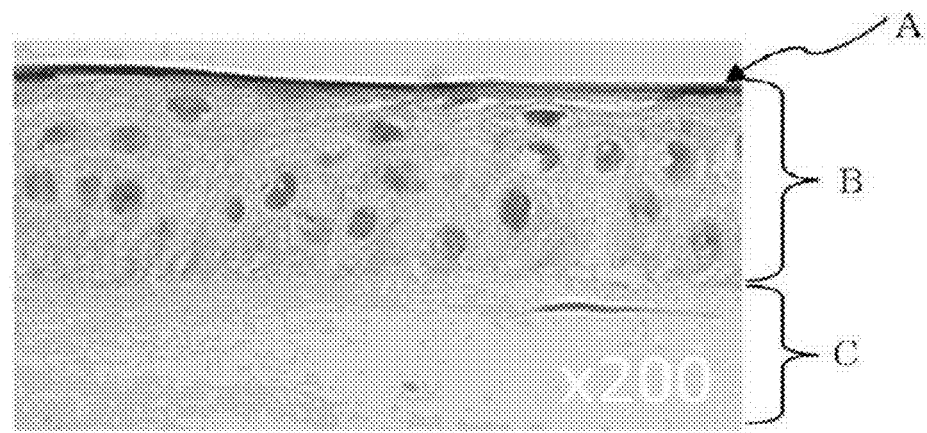
FIG. 2 is the enlarged figure of the cross-section surface of HE-stained human corneal epithelial sheet (observed at 200-fold magnification). A, B and C indicate superficial flattened cells, a cellular layer formed from cells derived from human corneal epithelial cells and an amnion substrate, respectively.

In addition, as the result of the observation of the cross section of the human corneal epithelial sheet under a microscope, it was found that the layer of the cultured cells covered more than 95% of the cross section of the sheet and more than 90% of the layer had the layered structures with more than double layer (FIG. 2-B) and most of the layered structures had 3 to 4 layers. It was also found that more than 90% of the surface of the layer of cultured cells were flattened cells (FIG. 2-A). This structure of the layer of the cultured cells including the flattened cells was similar to the corneal epithelium tissue which comprised non-keratinized stratified squamous epithelium with barrier functions.

[FACS Analysis]

Phosphate buffer saline, pH 7.4, containing BSA, powder (Sigma) was dissolved in purified water and filtered using a 0.22 μm filter to prepare 0.01 M phosphate buffer saline (pH 7.4) containing 2% BSA (0.138 M sodium chloride, 0.0027 M potassium chloride and 2% (w/v) bovine serum albumin. To the 2% BSA solution prepared, Triton X-100 (Wako Pure Chemical Industries Ltd.) was added to make the concentration of 0.1%. This was taken as BSA-T.

Antibody dilution was prepared as follows. To 485 μL of BSA-T, 10 μL of mouse IgG antibody solution (DAKO) and 5 μL of rabbit IgG antibody solution (DAKO) were added. The mixture was taken as the first antibody dilution for isotype control. In addition, to 486 μL of BSA-T, 10 μL of mouse anti-cytokeratin AE1AE3 antibody solution (DAKO) was added. It was taken as the first antibody dilution for detecting cytokeratin AE1AE3. Additionally, to 486 μL of BSA-T, 4 μL of rabbit anti-cytokeratin12 antibody solution (TransGenic) was added and it was taken as the first antibody dilution for detecting cytokeratin AE1AE3. Furthermore, to 998 μL of BSA-T, 2 μL of Alexa Fluor (registered trademark) 488-labeled goat anti-mouse IgG antibody solution (Life Technologies Japan) was added and it was taken as the second antibody dilution for detecting cytokeratin AE1AE3. In addition, to 998 μL of BSA-T, 2 μL of Alexa Fluor (registered trademark) 647-labeled goat anti-mouse IgG antibody solution (Life Technologies Japan) was added and it was taken as the second antibody dilution for detecting cytokeratin 12.

The insert membrane was removed from the ¼ sheet obtained by dividing from the above human corneal epithelial sheet. After the layer of the cultured cells and the amnion substrate were incubated with 0.25% trypsin solution (Life Technologies Japan) at 37° C. for 10 minutes, the KB+SHEM culture medium was added and only the cells which formed the cell layer were collected by pipetting. The cells collected were transferred to a centrifuge tube followed by centrifugation. The supernatant was removed. Then the cells were suspended with 1 mL of methanol (Wako Pure Chemical Industries Ltd.) which had been cooled to 4° C. and fixed for 10 minutes in a freezer (−20° C.). After the fixing, the cells were precipitated by centrifugation and methanol was removed. Then the cells were suspended by 1 mL of BSA-T and precipitated by centrifugation and BSA-T was removed. This washing process was repeated twice.

Then the cells were suspended by 4 mL of BSA-T and divided to 4 tubes with 1 mL in each tube. After the cells were precipitated by centrifugation, BSA-T was removed. Among the 4 tubes, two were used for isotype control, one for detecting cytokeratin AE1AE3 and the last for detecting cytokeratin 12. To each tube, 500 μL each of the first antibody dilution for isotype control, the first antibody dilution for detecting cytokeratin AE1AE3 and the first antibody dilution for detecting cytokeratin 12 were added respectively and the cells were suspended. The reaction was conducted at room temperature for 30 minutes. After reacting with the first antibody, the cells were precipitated by centrifugation and the first antibody dilutions were removed. Then the cells were suspended by adding 1 mL of BSA-T and precipitated by centrifugation. BSA-T was removed. This washing process was repeated three times. Then, to the tube for detecting cytokeratin AE1AE3, 500 μL of the second antibody dilution for detecting cytokeratin AE1AE3 was added. And to the tube for detecting cytokeratin 12, 500 μL of the second antibody dilution for detecting cytokeratin 12 was added. The cells were suspended and the reaction was conducted at room temperature for 30 minutes in lightproof condition. Meanwhile, to the two isotype control tubes, 500 μL each of the second antibody dilutions for detecting cytokeratin AE1AE3 and cytokeratin 12 was added respectively. The cells were suspended. These were taken as the control tubes for detecting cytokeratin AE1AE3 and cytokeratin 12, respectively, and reacted at room temperature for 30 minutes in lightproof condition. After reacting with the second antibody, the cells were precipitated by centrifugation and the second antibody dilutions were removed. Then the cells were suspended by adding 1 mL of BSA-T and precipitated by centrifugation and BSA-T was removed. This washing process was repeated three times. Finally, the cells were suspended by adding 500 μL of Propidium iodide solution, which was a 500-fold dilution with BSA-T, to each tube.

The cell suspensions in the tube for detecting cytokeratin AE1AE3 and its control tube were passed through a cell strainer. The ratio of positive cells of cytokeratin AE1AE3 was measured by comparing the intensity of the fluorescence originated from Alexa Fluor 488 pigment using BD FACS Canto (registered trademark, BD). In addition, the cell suspensions in the tube for detecting cytokeratin 12 and its control tube were passed through a cell strainer. The ratio of positive cells of cytokeratin 12 was measured by comparing the intensity of the fluorescence originated from Alexa Fluor 647 pigment using BD FACS Canto (registered trademark, BD).

[The Results of FACS Analysis]

Figure 3:
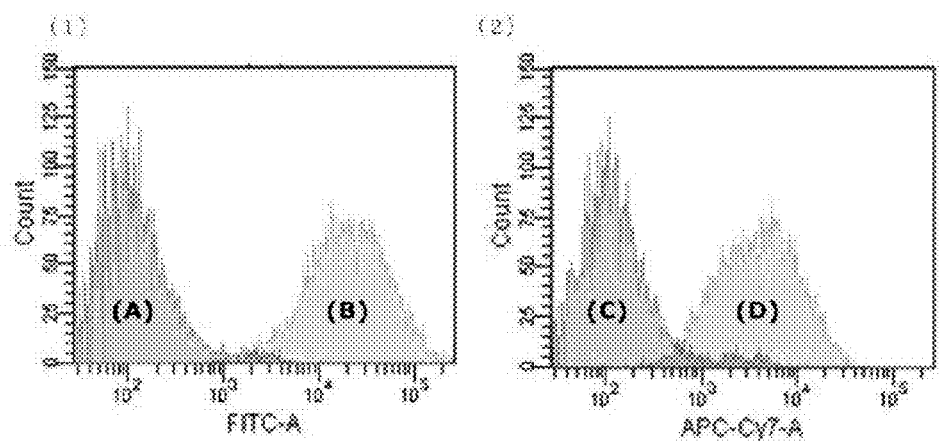
FIG. 3 (1) is the FACS analysis diagram of cytokeratin AE1/AE3-positive cells. The vertical axis represents the cell number, and the horizontal axis represents the fluorescence intensity derived from Alexa Fluor (registered trademark) 488 dye. (A) and (B) indicate the control and the fluorescence intensity of anti-cytokeratin AE1/AE3 antibody-stained cells, respectively.

As the result of FACS analysis, it was found that almost all (more than 99.99%) of the cells which formed the layer of the cultured cells on the amnion substrate were cytokeratin positive (FIG. 3-1) and more than 87% of the cells were cytokeratin 12 positive (FIG. 3-2).

[The Results of Quality Evaluation of Cell Sheet]

From the results of HE staining and FACS analysis, the existence of fibroblasts in the human corneal epithelial sheet which was produced by the method described above was not confirmed. And it shows the similar form with the corneal epithelium tissue which is comprised non-keratinized stratified squamous epithelium with barrier functions. Therefore, it can be applied suitably as a corneal epithelial sheet for transplantation.

[An Alternative Method of Primary Culture (P0 Culture) of Human Corneal Epithelial Cells]

Instead of using the method described above, the primary culture of human corneal epithelial cells was conducted by using the following method. From a human corneal tissue for laboratory use (a portion of two eyes, mfd. by SightLife, CnT-20 was used as preservative for the tissue.), sclera and conjunctiva were removed under a microscope using scalpels and scissors and, tissue sections including corneal epithelial and limbal tissues were detached. To the detached slice, CnT-20 medium (CELLEnTEC) containing 1.2 U/mL dispase solution (Sanko Junyaku) was added and it was allowed to stand at 4° C. for 15 to 20 hours. Then, after standing at 37° C. for 1 hour, the enzymatic reaction was terminated by addition of PBS containing 0.02% EDTA. The slice was transferred to a 35 mm dish (Prime Surface, Sumitomo Bakelite). Human corneal epithelial cells were detached from the tissue sections using tweezers under microscope and cell suspension was obtained. It was transferred to an Eppendorf tube (PROTEOSAVE, Sumitomo Bakelite) followed by centrifugation. After the supernatant was removed, CnT-20 medium was added to the pellet and centrifuged again. The cells were collected and then suspended by 1 mL of CnT-20 medium (the first medium in working examples) containing 10 μM of Y27632 (a ROCK inhibitor, Sigma) and 100 μM of 3-isobutyl-1-methylxanthine (an IBMX, phosphodiesterase inhibitor, Sigma). A portion of the cell suspension was taken and stained by a 10-fold dilution with Trypan Blue Stain (Life Technologies). After the cell count was measured, CnT-20 medium was added to the cell suspension so that the cell concentration was $2 \times 10^5$ cells/mL.

A 6-well cell culture insert (pore size: 0.4 μm, culture area: 4.2 $cm^2$, made from polyethylene terephthalate, BD Falcon Cell Culture Insert, BD Biosciences) coated with FNC Coating Mix (AthenaES) was allowed to stand in the 6-well companion plate added with the feeder cells described above. Then, to each well of the 6-well cell culture insert, 1.05 mL each of the cell suspension of human corneal epithelial cells collected above was added ($2 \times 10^5$ cells/well) and the culture was started. 3 to 5 hours after the beginning of the culture, to the 6-well cell culture insert, 0.5 mL of CnT-20 medium containing 10 μM of Y27632 (a ROCK inhibitor, Sigma) and 100 μM of 3-isobutyl-1-methylxanthine (a IBMX, phosphodiesterase inhibitor, Sigma) was added and cultured further for 2 to 3 days. Then the medium was replaced with CnT-20 medium containing 100 μM of 3-isobutyl-1-methylxanthine (an IBMX, phosphodiesterase inhibitor, Sigma), 1 μM of SB203580 (a MAP kinase inhibitor, Sigma) and 1 μM of SB431542 (a TGF-β receptor inhibitor, Sigma), which was designated as the second medium in working examples. The cells were cultured by changing the medium every 2 to 3 days. If changes in the feeder cells in the bottom wells, such as significant stripping from the bottom wells, were observed during this period, another 6-well companion plate in which the feeder cells were adhered in the bottom wells would be prepared and the 6-well cell culture insert would be transferred to it and the culture was continued. The culture of the cells including the following procedures was conducted at 37° C. in existence of 5% $CO_2$. The schema of the culture vessel setting in the primary culture of human corneal epithelial cells is shown in FIG. 4. The 6-well companion plate (the culture vessel) shown in FIG. 4, was separated into a lower side chamber (or the first chamber) and an upper side chamber (or the second chamber) by a membrane having micropores. To the first chamber human mesenchymal stem cells were added as feeder cells, while to the second chamber human corneal epithelial cells were added. The human mesenchymal stem cells adhered at the bottom of the culture vessel in the first chamber, while the human corneal epithelial cells were cultured in the second chamber on the surface of the membrane having micropores.

Figure 5:
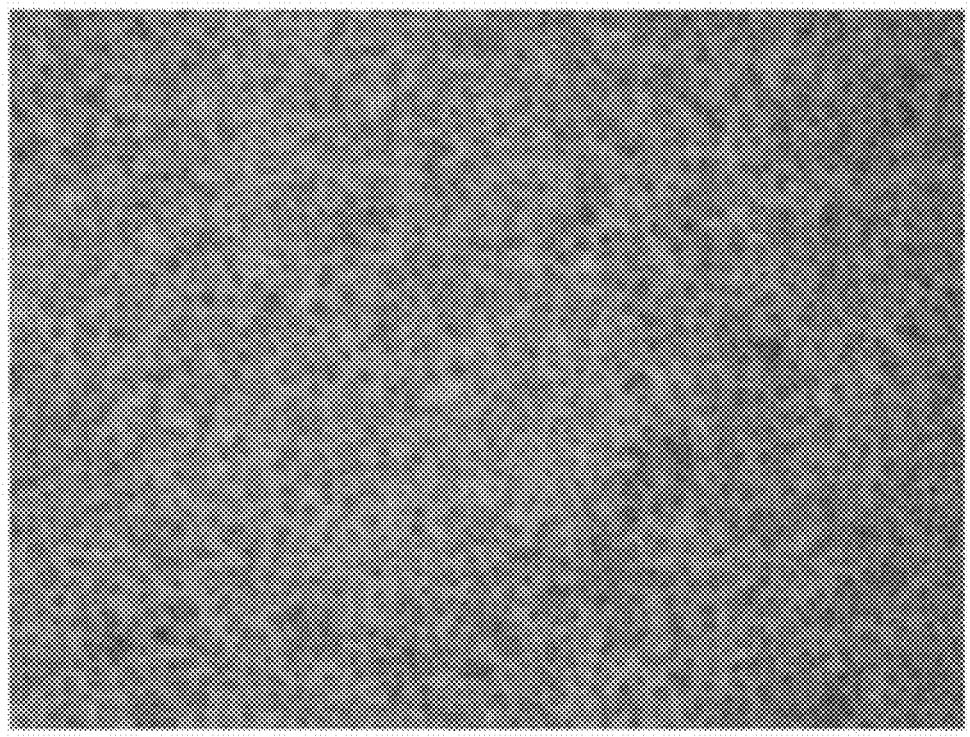
FIG. 5 is the enlarged figure of the surface of HE-stained human corneal epithelial sheet produced using the human corneal epithelial-derived cells obtained by the alternative method (observed at 100-fold magnification).
Figure 6:
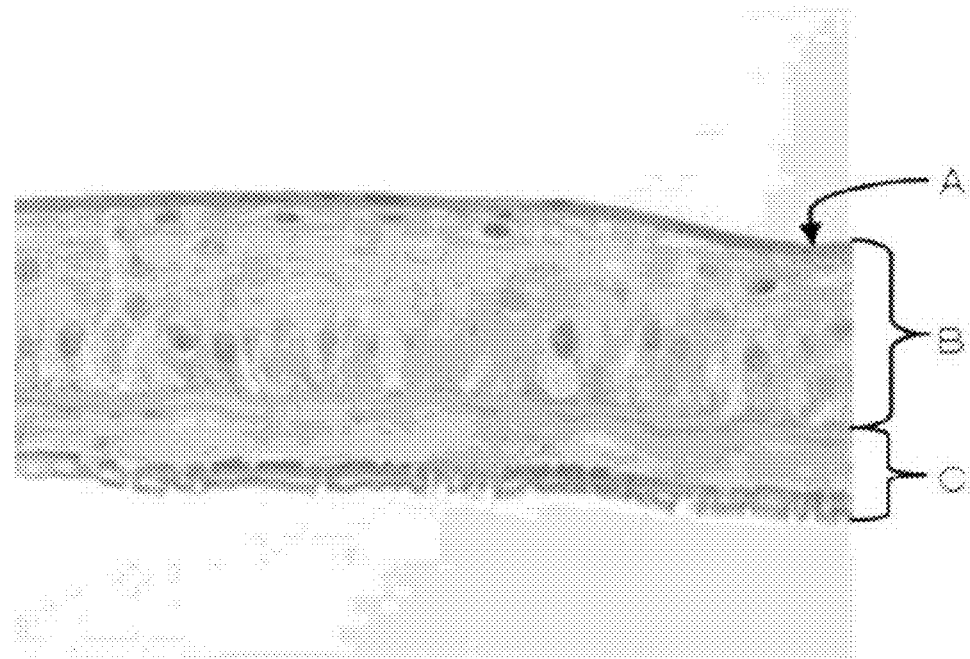
FIG. 6 is the enlarged figure of the surface of HE-stained human corneal epithelial sheet produced using the human corneal epithelial-derived cells obtained by the alternative method (observed at 200-fold magnification). A, B and C indicate superficial flattened cells, a cellular layer formed from cells derived from human corneal epithelial cells and an amnion substrate, respectively.

Using the human corneal epithelial-derived cells obtained by using the alternative method described above, the human corneal epithelial sheet produced by using the above method was HE stained and its surface was observed under microscope. As the result, the existence of fibroblasts could not be confirmed (FIG. 5). Since there were at least 1000 cells in the visual field of the microscope, the ratio of the fibroblast in the human corneal epithelial-derived cells was less than 0.1%. In addition, it was found that in the visual field of the microscope, more than 99.5% of the area of the surface of amnion substrate was covered by the layer of cultured cells and more than 95% of the layer of cultured cells had the layered structures with more than 4 layers (FIG. 6-B). In addition, it was found that more than 90% of the surface of the layer of the cells cultured was covered by flattened cells (FIG. 6-A). This structure of the layer of the cultured cells including the flattened cells was similar to the corneal epithelium tissue which comprised non-keratinized stratified squamous epithelium with barrier functions.

[Investigation of Promoting Effects of the Combination of a MAP Kinase Inhibitor and a TGF-β Receptor Inhibitor on the Proliferation of Human Corneal Epithelial Cells During their Culture]

The human corneal epithelial-derived cells which had been cryopreserved above were thawed quickly in an incubator at 37° C. and suspended by adding CnT-20 medium. The cells were collected by centrifugation and suspended by CnT-20 medium. It was taken as the cell suspension and its viable cell count was measured. Then the cell suspension was added to a 96-well plate coated with FNC Coating Mix (AthenaES) so that the viable cell count was 3500 cells/well. Furthermore, a MAP kinase inhibitor and a TGF-β receptor inhibitor were added to these wells in the medium in combinations and the concentrations of groups (1) to (5) shown in Table 9. The combinations and the concentrations of MAP kinase inhibitor and TGF-β receptor inhibitor in the groups were (1) SB203580 (1 μM)+SB431542 (1 μM), (2) SB203580 (1 μM)+A83-01 (10 μM), (3) SB203580 (1 μM)+LY364947 (10 μM), (4) SB239063 (10 μM)+SB431542 (1 μM), (5) SB239063 (10 μM)+A83-01 (10 μM) and (6) SB239063 (10 μM)+LY364947 (10 μM). And those without the addition of a MAP kinase inhibitor and a TGF-β receptor inhibitor were taken as the controls. 5 days after the beginning of the culture, 10 μL of Cell Counting Kit-8 (CCK-8) solution containing water soluble tetrazolium salt (WST-8) was added as a color reagent to the medium. One hour later, the absorbance (OD450) at the wavelength of 450 nm was measured using a plate reader. The measurements of 4 wells were conducted in each case of the combinations and the average values of the controls were taken as 100%. The measured values in each group were calculated by comparison with the controls. It should be noted that the viable cell count is known to be proportional with the absorbance obtained by this method.

Figure 7:
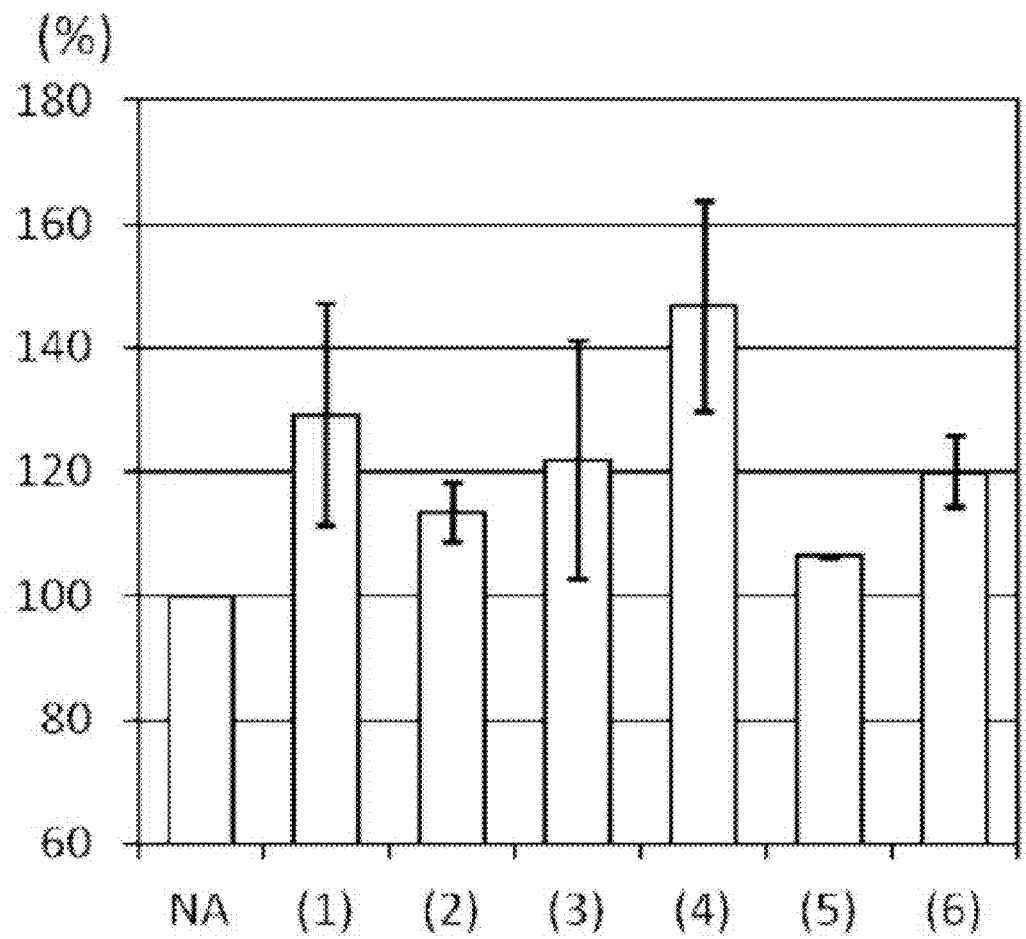
FIG. 7 shows the human corneal epithelial cell proliferation-promoting effects of the combination of various MAP kinase inhibitors and TGF-β receptor inhibitors during the incubation of the human corneal epithelial cells. The vertical axis represents the relative value (%) of the absorbance of each group against the absorbance (OD450) of the control group (NA) being 100%. An error bar indicates standard deviation.

As the results, the values of the measurements in all the groups, including groups (1) to (6), were over 100% compared with the controls. It shows that the proliferation of human corneal epithelial cells was promoted by the combinational additions of a MAP kinase inhibitor and a TGF-β receptor inhibitor (FIG. 7). Besides, in groups (1) SB203580 (1 μM)+SB431542 (1 μM), (3) SB203580 (1 μM)+

LY364947 (10 µM), (4) SB239063 (10 µM)+SB431542 (1 µM) and (6) SB239063 (10 µM)+LY364947 (10 µM), the measured values were over 120%. It shows that the proliferation of human corneal epithelial cells was especially promoted by these combinational additions of a MAP kinase inhibitor and a TGF-β receptor inhibitor (FIG. 7). In addition, the value in group (1) SB203580 (1 µM)+SB431542 (1 µM) was about 130% and that in group (4) SB239063 (10 µM)+SB431542 (1 µM) was over 130%. It shows that the promotion effects were especially remarkable in cases of these combinations (FIG. 7).

TABLE 9

| | MAP kinase inhibitor, TGF-β receptor inhibitor and their concentrations | |
|---|---|---|
| Number of combination | MAP kinase inhibitor (Concentration) | TGF-β receptor inhibitor (Concentration) |
| (1) | SB203580 (1 µM) | SB431542 (1 µM) |
| (2) | SB203580 (1 µM) | A38-01 (10 µM) |
| (3) | SB203580 (1 µM) | LY364947 (10 µM) |
| (4) | SB239063 (10 µM) | SB431542 (1 µM) |
| (5) | SB239063 (10 µM) | A38-01 (10 µM) |
| (6) | SB239063 (10 µM) | LY364947 (10 µM) |

INDUSTRIAL APPLICABILITY

The present invention enables to provide stably the human corneal epithelial sheets which have a constant quality and can be transplanted to patients with corneal diseases such as recurrent corneal dystrophy.

EXPLANATIONS OF SYMBOLS 1. 6-well cell culture insert
2. 6-well companion plate (culture vessel)
3. membrane having micropores
4. human corneal epithelial cells
5. feeder cells (human mesenchymal stem cells)
6. the first chamber
7. the second chamber
8. bottom wells

The invention claimed is:

1. A method for producing cells derived from human corneal epithelial cells, which comprises a process wherein, in a culture vessel separated into first and second chambers by a membrane having micropores that disallow cells to pass through, feeder cells are added to the first chamber and human corneal epithelial cells are added to the second chamber, said human corneal epithelial cells are cultured on the membrane having micropores by using a first medium containing a Rho-associated protein kinase (ROCK) inhibitor and a phosphodiesterase inhibitor, but not containing a mitogen-activated protein (MAP) kinase inhibitor and a TGF-β receptor inhibitor, and then said human corneal epithelial cells are cultured by using a second medium containing a phosphodiesterase inhibitor, a mitogen-activated protein (MAP) kinase inhibitor, and a TGF-β receptor inhibitor, but not containing a Rho-associated protein kinase (ROCK) inhibitor.

2. The method according to claim 1, wherein said culture vessel is separated by the membrane having micropores into two chambers up and down, so as to give an upper chamber and a lower chamber.

3. The method according to claim 2, wherein said lower chamber is the first chamber and said upper chamber is the second chamber.

4. The method according to claim 3, wherein said human corneal epithelial cells are cultured on the membrane having micropores that disallow said cells to pass through and retained in said culture vessel without direct contact with the feeder cells.

5. The method according to claim 1, wherein the ROCK inhibitor contained in said first medium is Y27632, the phosphodiesterase inhibitor contained in said first and second media is 3-isobutyl-1-methylxanthine, the MAP kinase inhibitor contained in said second medium is selected from SB203580, SB239063 and a combination thereof, and the TGF-β receptor inhibitor contained in said second medium is selected from SB431542, LY364947, A83-01 and a combination thereof.

6. The method according to claim 1, wherein the ROCK inhibitor contained in said first medium is Y27632, the phosphodiesterase inhibitor contained in said first and second media is 3-isobutyl-1-methylxanthine, the MAP kinase inhibitor contained in said second medium is SB203580, and the TGF-β receptor inhibitor contained in said second medium is SB431542.

7. The method according to claim 6, wherein the concentrations of Y27632 contained in said first medium, 3-isobutyl-1-methylxanthine contained in said first and second media, SB203580 contained in said second medium, and SB431542 contained in said second medium are 1 to 20 µM, 50 to 150 µM, 0.2 to 2 µM, and 0.2 to 2 µM, respectively.

8. The method according to claim 6, wherein the concentrations of Y27632 contained in said first medium, 3-isobutyl-1-methylxanthine contained in said first and second media, SB203580 contained in said second medium, and SB431542 contained in said second medium are about 10 µM, about 100 µM, about 1 µM, and about 1 µM, respectively.

9. The method according to claim 1, wherein said feeder cells are human mesenchymal stem cells.

10. The method of claim 1, wherein the method further comprises a step wherein the cells obtained by the method according to claim 1 are frozen by suspending in a cell-freezing liquid, so as to obtain frozen cells.

11. A method for producing human corneal epithelial sheet, which comprises a step wherein, after thawing the cells derived from the human corneal epithelial cells obtained by the method according to claim 10, the cells are cultured in a culture vessel containing feeder cells on an amnion substrate which is placed on the membrane having micropores that disallow said feeder cells to pass through and retained in said culture vessel with a third medium containing a ROCK inhibitor, and then cultured by using a fourth medium containing a MAP kinase inhibitor and a TGF-β receptor inhibitor, so as to form a cell layer comprising the cells derived from said human corneal epithelial cells on said amnion substrate, and a subsequent step wherein said cell layer is cultured by using said fourth medium in a condition where all or part of the surface of said cell layer is not covered with the medium.

12. The method according to claim 11, wherein said amnion substrate is placed in said culture vessel with the side stripping off the amnion epithelium facing upward.

13. The method according to claim 11, wherein said ROCK inhibitor contained in said third medium is Y27632, said MAP kinase inhibitor contained in said fourth medium is SB203580, and said TGF-β receptor inhibitor contained in said fourth medium is SB431542.

14. The method according to claim 13, wherein the concentrations of Y27632 contained in said third medium, SB203580 contained in said fourth medium, and SB431542 contained in said fourth medium are 1 to 20 µM, 0.2 to 2 µM, and 0.2 to 2 µM, respectively.

15. The method according to claim 13, wherein the concentrations of Y27632 contained in said third medium, SB203580 contained in said fourth medium, and SB431542 contained in said fourth medium are about 10 µM, 1 µM, and about 1 µM, respectively.

16. The method according to claim 11, wherein said feeder cells are human mesenchymal stem cells.

* * * * *